United States Patent
Sylvestre et al.

(10) Patent No.: US 8,415,462 B2
(45) Date of Patent: Apr. 9, 2013

(54) SIGNALING PEPTIDES

(75) Inventors: Nathalie Sylvestre, Ergersheim (FR); Eric Jacobs, Stotzheim (FR)

(73) Assignee: Transgene S.A., Illkirch (FR)

( * ) Notice: Subject to any disclaimer, the term of this patent is extended or adjusted under 35 U.S.C. 154(b) by 0 days.

(21) Appl. No.: 12/600,460

(22) PCT Filed: Jan. 29, 2008

(86) PCT No.: PCT/EP2008/051035
§ 371 (c)(1),
(2), (4) Date: Nov. 16, 2009

(87) PCT Pub. No.: WO2008/138649
PCT Pub. Date: Nov. 20, 2008

(65) Prior Publication Data
US 2010/0160227 A1    Jun. 24, 2010

(30) Foreign Application Priority Data

May 15, 2007   (EP) .................................... 07360020

(51) Int. Cl.
| | | |
|---|---|---|
| *C07H 21/04* | (2006.01) | |
| *C12N 15/00* | (2006.01) | |
| *C12Q 1/00* | (2006.01) | |
| *C12P 21/06* | (2006.01) | |

(52) U.S. Cl. ........ 536/23.4; 435/320.1; 435/4; 435/69.1
(58) Field of Classification Search .................... 530/300
See application file for complete search history.

(56) References Cited

U.S. PATENT DOCUMENTS

2005/0159386 A1* 7/2005 Kieny et al. .................... 514/44

FOREIGN PATENT DOCUMENTS

| EP | 1 275 716 A | 1/2003 |
|---|---|---|
| JP | 06 141873 A | 5/1994 |
| JP | 10 023899 A | 1/1998 |
| WO | WO 99/03885 A | 1/1999 |
| WO | WO 2008/092854 | 8/2008 |
| WO | WO 2008/138648 | 11/2008 |

OTHER PUBLICATIONS

Database EMBL Tango et al., Rabies virus strain PG glycoprotein mRNA, complete cds., 2000, accession No. AY009097.*
Database EMBL Zhao et al., VGLG_RABVD, 2006, accession No. QOGBX6.*
Andrew et al., "The Immunogenicity of VP 7, a Rotavirus Antigen Resident in the Endoplasmic Reticulum, is Enhanced by Cell Surface Expression", Journal of Virology, Oct. 1990, pp. 4776-4783, vol. 64, No. 10, Am. Society for Microbiology.
Ji et al., "Targeting Human Papillomavirus Type 16 E7 to the Endosomal/Lysosomal Compartment Enhances the Antitumor Immunity of DNA Vaccines against Murine Human Papillomavirus Type 16 E7-Expressing Tumors", Human Gene Therapy, Nov. 1999, pp. 2727-2740, vol. 10, Mary Ann Liebert, Inc.
Matzke et al., "Inactivation of Repeated Genes—DNA-DAN Interaction?", J. Passkowski (ed.) Homologous Recombination and Gene Silencing in Plants, 1994, pp. 271-307, Kluwer Academic Publishers, Netherlands.
Xianhe et al., "Comparisons of nucleotide and deduced amino acid sequences of the glycoprotein genes of a Chinese street strain (CGX89-1) and a Chinese vaccine strain (3aG) of rabies virus", Virus Research, 1993, pp. 101-112, Elseview Science Publishers B.V.
Anilionis et al., "Rabies virus glycoprotein mRNA complete cds", GenBank:M38452.1, Aug. 1993, pp. 1-2.
Anilionis et al., "Amino-Acid Sequence of the Rabies Virus Glyco Protein Deduces From its Clones Gene," Comparative Immunology Microbiology and Infectious Diseases, 1982, vol. 5, Nos. 1-3, pp. 27-32, XP002481354, Elsevier B.V., Amsterdam, Holland.
Tango et al., "Rabies virus strain PG glycoprotein mRNA, complete cds," Database EMBL, E.B.I. Hinxton U.K., Dec. 5, 2000, XP002501085, Database Accession No. AY009097.
Xianhe et al., "Rabies virus chinese vaccine strain glycoprotein gene sequence," Database EMBL, E.B.I. Hinton U.K., Oct. 20, 1992, XP002501086, Database Accession No. L04522.
Sakamoto et al., "G-glycoprotein G (rabies virus, Nishigahara, Genomic RNA, 2083 nt) G-glycoprotein G [rabies virus, Nishigahara, Genomic RNA, 2083 nt]," Jan. 30, 1995, XP002501087, Database Accession No. S72465.
Nadin-Davis et al., "Rabies virus strain Arctic fox isolate 90RABN9339 glycoprotein (GE) gene, partial cds," Database EMBL:, Jul. 21, 1994, XP002501088, Database Accession No. U11751.

* cited by examiner

*Primary Examiner* — Zachariah Lucas
*Assistant Examiner* — Barry A Chestnut
(74) *Attorney, Agent, or Firm* — Buchanan Ingersoll & Rooney PC

(57) ABSTRACT

The present invention provides novel peptides of specified sequence and their use as a signal peptide or a membrane-anchoring peptide. It also relates to chimeric polypeptide comprising one or more such peptides and a polypeptide of interest as well as nucleic acid molecules, vectors, infections vital particles and host cells encoding such peptides and chimeric polypeptides. The present invention also relates to a pharmaceutical composition comprising such elements and a pharmaceutically acceptable vehicle. The present invention also provides a method for recumbently producing a polypeptide using such peptides, especially for directing expression of a polypeptide of interest extracellularly or anchored at the surface of the plasma membrane.

23 Claims, No Drawings

SEQUENCE LISTING

<160> NUMBER OF SEQ ID NOS: 28

<210> SEQ ID NO 1
<211> LENGTH: 23
<212> TYPE: PRT
<213> ORGANISM: artificial sequence
<220> FEATURE:
<223> OTHER INFORMATION: signal peptide derived from the rabies
      glycoprotein of ERA strain (M38452 v1)

<400> SEQUENCE: 1

Met Val Pro Gln Val Leu Leu Phe Val Pro Leu Leu Gly Phe Pro Leu
1               5                   10                  15

Cys Phe Gly Lys Phe Pro Ile
            20

<210> SEQ ID NO 2
<211> LENGTH: 23
<212> TYPE: PRT
<213> ORGANISM: artificial sequence
<220> FEATURE:
<223> OTHER INFORMATION: signal peptide derived from the rabies
      glycoprotein of PG strain (ay009097, v1)

<400> SEQUENCE: 2

Met Val Pro Gln Ala Leu Leu Leu Val Pro Leu Leu Gly Phe Ser Leu
1               5                   10                  15

Cys Phe Gly Lys Phe Pro Ile
            20

<210> SEQ ID NO 3
<211> LENGTH: 66
<212> TYPE: PRT
<213> ORGANISM: artificial sequence
<220> FEATURE:
<223> OTHER INFORMATION: membrane-anchoring peptide derived from the
      rabies Glycoprotein of PG strain (M38452 v2-ay009097 v1)

<400> SEQUENCE: 3

Tyr Val Leu Leu Ser Ala Gly Thr Leu Ile Ala Leu Met Leu Ile Ile
1               5                   10                  15

Phe Leu Ile Thr Cys Cys Lys Arg Val Asp Arg Pro Glu Ser Thr Gln
                20                  25                  30

Arg Ser Leu Arg Gly Thr Gly Arg Asn Val Ser Val Thr Ser Gln Ser
            35                  40                  45

Gly Lys Phe Ile Ser Ser Trp Glu Ser His Lys Ser Gly Gly Glu Thr
        50                  55                  60

Arg Leu
65

<210> SEQ ID NO 4
<211> LENGTH: 66
<212> TYPE: PRT
<213> ORGANISM: artificial sequence
<220> FEATURE:
<223> OTHER INFORMATION: membrane-anchoring peptide derived from the
      rabies glycoprotein of Nishigahara strain (S72465, v1)

<400> SEQUENCE: 4

Tyr Val Leu Leu Ser Ala Gly Thr Leu Ile Ala Leu Met Leu Ile Ile
1               5                   10                  15

Phe Leu Met Thr Cys Cys Arg Lys Val Asp Arg Pro Glu Ser Thr Gln
                20                  25                  30

```
Arg Ser Leu Arg Gly Thr Gly Arg Asn Val Ser Val Thr Ser Gln Ser
        35                  40                  45

Gly Lys Phe Ile Ser Ser Trp Glu Ser His Lys Ser Gly Gly Glu Thr
    50                  55                  60

Arg Leu
65

<210> SEQ ID NO 5
<211> LENGTH: 66
<212> TYPE: PRT
<213> ORGANISM: artificial sequence
<220> FEATURE:
<223> OTHER INFORMATION: membrane-anchoring peptide derived from the
      rabies glycoprotein of artic fox strain (U11751, v1)

<400> SEQUENCE: 5

Tyr Val Leu Ile Ile Ala Gly Val Leu Ile Ala Met Ile Leu Thr Ile
1               5                   10                  15

Phe Leu Met Thr Cys Cys Gly Arg Gly Asn Arg Pro Lys Ser Thr Gln
                20                  25                  30

His Ser Leu Gly Gly Ile Gly Arg Lys Val Ser Ala Thr Ser Gln Ser
        35                  40                  45

Gly Lys Val Ile Ser Ser Trp Glu Ser His Lys Ser Gly Gly Glu Thr
    50                  55                  60

Arg Leu
65

<210> SEQ ID NO 6
<211> LENGTH: 23
<212> TYPE: PRT
<213> ORGANISM: Rabies virus (ERA strain)

<400> SEQUENCE: 6

Met Val Pro Gln Ala Leu Leu Phe Val Pro Leu Leu Val Phe Pro Leu
1               5                   10                  15

Cys Phe Gly Lys Phe Pro Ile
                20

<210> SEQ ID NO 7
<211> LENGTH: 23
<212> TYPE: PRT
<213> ORGANISM: Rabies virus (PG strain)

<400> SEQUENCE: 7

Met Val Pro Leu Ala Leu Leu Val Pro Leu Leu Gly Phe Ser Leu
1               5                   10                  15

Cys Phe Gly Lys Phe Pro Ile
                20

<210> SEQ ID NO 8
<211> LENGTH: 66
<212> TYPE: PRT
<213> ORGANISM: Rabies virus (PG strain)

<400> SEQUENCE: 8

Tyr Val Leu Leu Ser Ala Gly Thr Leu Ile Ala Leu Met Leu Ile Ile
1               5                   10                  15

Phe Leu Ile Thr Cys Cys Lys Arg Val Asp Arg Pro Glu Ser Thr Gln
                20                  25                  30

Arg Ser Leu Arg Gly Thr Gly Arg Asn Val Ser Val Thr Ser Gln Ser
        35                  40                  45
```

Gly Lys Phe Ile His Ser Trp Glu Ser Tyr Lys Ser Gly Gly Glu Thr
    50                  55                  60

Gly Leu
65

<210> SEQ ID NO 9
<211> LENGTH: 66
<212> TYPE: PRT
<213> ORGANISM: Rabies virus (Nishigahara strain)

<400> SEQUENCE: 9

Tyr Val Leu Leu Ser Ala Gly Thr Leu Ile Ala Leu Met Leu Ile Ile
1               5                   10                  15

Phe Leu Met Thr Cys Cys Arg Lys Val Asp Arg Pro Glu Ser Thr Gln
            20                  25                  30

Arg Ser Leu Arg Gly Thr Gly Arg Asn Val Ser Val Thr Ser Gln Ser
        35                  40                  45

Gly Lys Phe Ile Pro Ser Trp Glu Ser Tyr Lys Ser Gly Gly Glu Thr
    50                  55                  60

Gly Leu
65

<210> SEQ ID NO 10
<211> LENGTH: 66
<212> TYPE: PRT
<213> ORGANISM: Rabies virus (artic fox strain)

<400> SEQUENCE: 10

Tyr Val Leu Ile Ile Ala Gly Val Leu Ile Ala Met Ile Leu Thr Ile
1               5                   10                  15

Phe Leu Met Thr Cys Cys Gly Arg Gly Asn Arg Pro Lys Ser Thr Gln
            20                  25                  30

His Ser Leu Gly Gly Ile Gly Arg Lys Val Ser Ala Thr Ser Gln Ser
        35                  40                  45

Gly Lys Val Ile Ser Ser Trp Glu Ser Tyr Lys Ser Gly Gly Glu Thr
    50                  55                  60

Arg Leu
65

<210> SEQ ID NO 11
<211> LENGTH: 69
<212> TYPE: DNA
<213> ORGANISM: artificial sequence
<220> FEATURE:
<223> OTHER INFORMATION: degenerated nucleotide sequence encoding the
      signal peptide M38452, v1 derived from the rabies glycoprotein
      (ERA strain)

<400> SEQUENCE: 11
atggtgccac aggtactact ctttgtgcca ttgctcgggt ttccgttatg tttcggcaag    60
ttcccgatc                                                             69

<210> SEQ ID NO 12
<211> LENGTH: 69
<212> TYPE: DNA
<213> ORGANISM: artificial sequence
<220> FEATURE:
<223> OTHER INFORMATION: degenerated nucleotide sequence encoding the
      peptide signal ay009097, v1 derived from the rabies glycoprotein
      of PG strain

<400> SEQUENCE: 12

```
atggtaccac aagcgctgtt acttgtccca ctgcttggtt tctctttatg ttttggaaaa      60
ttcccaata                                                              69
```

<210> SEQ ID NO 13
<211> LENGTH: 69
<212> TYPE: DNA
<213> ORGANISM: artificial sequence
<220> FEATURE:
<223> OTHER INFORMATION: degenerated nucleotide sequence encoding the
      signal peptide of the rabies glycoprotein of the Nishigahara
      strain (S72465, v1)

<400> SEQUENCE: 13

```
atggtccctc aagcactact tctagttccg atcctaggat tctcctcgtg cttcggtaaa      60
tttccgatt                                                              69
```

<210> SEQ ID NO 14
<211> LENGTH: 69
<212> TYPE: DNA
<213> ORGANISM: artificial sequence
<220> FEATURE:
<223> OTHER INFORMATION: degenerated nucleotide sequence encoding the
      signal peptide derived from the rabies glycoprotein of artic fox
      strain (u11751, v1)

<400> SEQUENCE: 14

```
atggtgcccc aggttctttt gttcgtgcct ctacttggct tcccccttg ttttggcaag      60 tttccgatc                                                              69
```

<210> SEQ ID NO 15
<211> LENGTH: 69
<212> TYPE: DNA
<213> ORGANISM: artificial sequence
<220> FEATURE:
<223> OTHER INFORMATION: degenerated nucleotide sequence encoding a
      signal peptide derived from the rabies glycoprotein of artic fox
      strain (u11751, v2)

<400> SEQUENCE: 15

```
atggtaccctc aagtcttatt gttcgtaccg ttgttaggtt tcccgttatg ctttggcaaa     60
tttccaata                                                              69
```

<210> SEQ ID NO 16
<211> LENGTH: 69
<212> TYPE: DNA
<213> ORGANISM: artificial sequence
<220> FEATURE:
<223> OTHER INFORMATION: degenerated nucleotide sequence encoding a
      signal peptide Derived from the rabies glycoprotein of ERA strain
      (M38452, v2-ay009097 v2)

<400> SEQUENCE: 16

```
atggtaccgc aagccctgct attcgtacct ttattggtct tccctctg tttcggtaag       60 tttcctata                                                              69
```

<210> SEQ ID NO 17
<211> LENGTH: 201
<212> TYPE: DNA
<213> ORGANISM: artificial sequence
<220> FEATURE:
<223> OTHER INFORMATION: degenerated nucleotide sequence encoding a
      membrane-Anchoring peptide derived from the rabies glycoprotein
      of ERA strain (M38452, v1)

<400> SEQUENCE: 17

```
tacgttttgc tcagcgcggg tgctcttacg gcgctgatgt tgattatctt tctcatgact    60
tgttgccgca gagtgaaccg ttcggagccg actcagcata acttacgtgg cactggcaga   120
gaagttagtg ttacaccaca gtccggaaaa attatctcca gctgggagtc tcataaatcg   180
ggcggagaaa cgaggctatg a                                              201
```

<210> SEQ ID NO 18
<211> LENGTH: 201
<212> TYPE: DNA
<213> ORGANISM: artificial sequence
<220> FEATURE:
<223> OTHER INFORMATION: degenerated nucleotide sequence encoding a
      membrane-anchoring peptide derived from the rabies glycoprotein
      of PG strain (ay009097, v1)

<400> SEQUENCE: 18

```
tatgttcttc tctctgctgg aactttaata gctttaatgt taataatatt cttaataacg    60
tgctgtaaaa gggtagaccg tccagagtca actcagcgca gccttagggg tactgggaga   120
aatgtttccg tgacatcaca gagtggaaaa tttatctcgt cttgggaatc tcataagagt   180
ggaggcgaaa cacgtctttg a                                              201
```

<210> SEQ ID NO 19
<211> LENGTH: 201
<212> TYPE: DNA
<213> ORGANISM: artificial sequence
<220> FEATURE:
<223> OTHER INFORMATION: degenerated nucleotide sequence encoding a
      membrane-anchoring peptide derived from the rabies glycoprotein
      of Nishigahara strain (S72465, v1)

<400> SEQUENCE: 19

```
tacgtgctcc taagcgcggg caccttgatt gcactcatgc tgatcatatt cctaatgacg    60
tgttgcagga aagtggatcg gcctgaatcg acacaacgaa gtctaagagg aacgggtcgg   120
aacgtctctg taacctccca atccggcaaa ttcatatcaa gttgggaaag tcacaagagc   180
ggtggtgaga ctcgactatg a                                              201
```

<210> SEQ ID NO 20
<211> LENGTH: 201
<212> TYPE: DNA
<213> ORGANISM: artificial sequence
<220> FEATURE:
<223> OTHER INFORMATION: degenerated nucleotide sequence encoding a
      membrane-anchoring peptide derived from the rabies glycoprotein
      of artic fox strain (u11751, v1)

<400> SEQUENCE: 20

```
tacgtcttga taattgccgg tgtcctaatc gcgatgatac tcacaatctt ccttatgacc    60
tgctgtggaa gaggtaaccg ccccaagtcc acccagcatt ctctgggagg tataggacgt   120
aaggtatcgg ccacgtctca gtctggtaag gtcatttcct cgtgggagtc ccataaaagc   180
ggcggggaaa ctagactctg a                                              201
```

<210> SEQ ID NO 21
<211> LENGTH: 201
<212> TYPE: DNA
<213> ORGANISM: artificial sequence
<220> FEATURE:
<223> OTHER INFORMATION: degenerated nucleotide sequence encoding a
      membrane-anchoring peptide derived from the rabies glycoprotein
      of artic fox strain (u11751, v2)

<400> SEQUENCE: 21

```
tatgtgctta tcatcgcggg agtactcatt gctatgatcc taactatatt tcttatgact    60
tgctgcggtc gagggaatag accaaaaagc acacaacact cgctgggcgg aatcggtcga   120
aaagtctcag caactagtca atcaggaaaa gttataagct cctgggaaag ccacaagtct   180
ggaggtgaga ctagactatg a                                              201

<210> SEQ ID NO 22
<211> LENGTH: 201
<212> TYPE: DNA
<213> ORGANISM: artificial sequence
<220> FEATURE:
<223> OTHER INFORMATION: degenerated nucleotide sequence encoding a
      membrane-anchoring peptide derived from the rabies glycoprotein
      of PG strain (M38452, v2-ay009097, v2)

<400> SEQUENCE: 22
tacgtactgc tatcggcagg cacgttgatc gcactaatgc ttatcatctt cctaataacc    60
tgctgcaagc gggttgatag gcccgaaagt acccaaaggt ccttgagagg taccggacgc   120
aacgtatcgg taacgtcgca aagcggcaag ttcattagca gttgggagtc gcacaaatca   180
ggtggagaga cccgcctgtg a                                              201

<210> SEQ ID NO 23
<211> LENGTH: 276
<212> TYPE: DNA
<213> ORGANISM: artificial sequence
<220> FEATURE:
<223> OTHER INFORMATION: degenerated nucleotide sequence encoding signal
      and membrane-anchoring peptides derived from the rabies
      glycoprotein of ERA strain (M38452, v1)

<400> SEQUENCE: 23
atggtgccac aggtactact ctttgtgcca ttgctcgggt ttccgttatg tttcggcaag    60
ttcccgatcg gatcctacgt tttgctcagc gcgggtgctc ttacggcgct gatgttgatt   120
atctttctca tgacttgttg ccgcagagtg aaccgttcgg agccgactca gcataactta   180
cgtggcactg gcagagaagt tagtgttaca ccacagtccg gaaaaattat ctccagctgg   240
gagtctcata aatcgggcgg agaaacgagg ctatga                              276

<210> SEQ ID NO 24
<211> LENGTH: 276
<212> TYPE: DNA
<213> ORGANISM: artificial sequence
<220> FEATURE:
<223> OTHER INFORMATION: degenerated nucleotide sequence encoding signal
      and membrane-anchoring peptides derived from the rabies
      glycoprotein of PG strain (ay009097, v1)

<400> SEQUENCE: 24
atggtaccac aagcgctgtt acttgtccca ctgcttggtt tctctttatg ttttggaaaa    60
ttcccaatag gatcctatgt tcttctctct gctggaactt aatagctttt aatgttaata   120
atattcttaa taacgtgctg taaaagggta gaccgtccag agtcaactca gcgcagcctt   180
aggggtactg ggagaaatgt ttccgtgaca tcacagagtg gaaaatttat ctcgtcttgg   240
gaatctcata agagtggagg cgaaacacgt ctttga                              276

<210> SEQ ID NO 25
<211> LENGTH: 276
<212> TYPE: DNA
<213> ORGANISM: artificial sequence
<220> FEATURE:
<223> OTHER INFORMATION: degenerated nucleotide sequence encoding signal
``` and membrane-anchoring peptides derived from the rabies
glycoprotein of Nishigahara strain (S72465, v1)

<400> SEQUENCE: 25
atggtccctc aagcactact tctagttccg atcctaggat tctcctcgtg cttcggtaaa        60
tttccgattg gatcctacgt gctcctaagc gcgggcacct tgattgcact catgctgatc      120
atattcctaa tgacgtgttg caggaaagtg gatcggcctg aatcgacaca acgaagtcta      180
agaggaacgg gtcggaacgt ctctgtaacc tcccaatccg gcaaattcat atcaagttgg      240
gaaagtcaca gagcggtgg tgagactcga ctatga                                 276

<210> SEQ ID NO 26
<211> LENGTH: 276
<212> TYPE: DNA
<213> ORGANISM: artificial sequence
<220> FEATURE:
<223> OTHER INFORMATION: degenerated nucleotide sequence encoding signal
      and membrane-anchoring peptides derived from the rabies
      glycoprotein of artic fox strain (u11751, v1)

<400> SEQUENCE: 26
atggtgcccc aggttctttt gttcgtgcct ctacttggct tcccccttg ttttggcaag        60 tttccgatcg gatcctacgt cttgataatt gccggtgtcc taatcgcgat gatactcaca      120
atcttcctta tgacctgctg tggaagaggt aaccgcccca gtccaccca gcattctctg       180 ggaggtatag gacgtaaggt atcggccacg tctcagtctg gtaaggtcat ttcctcgtgg      240
gagtcccata aaagcggcgg ggaaactaga ctctga                                276

<210> SEQ ID NO 27
<211> LENGTH: 276
<212> TYPE: DNA
<213> ORGANISM: artificial sequence
<220> FEATURE:
<223> OTHER INFORMATION: degenerated nucleotide sequence encoding signal
      and membrane-anchoring peptides derived from the rabies
      glycoprotein of artic fox strain (u11751, v2)

<400> SEQUENCE: 27
atggtacctc aagtcttatt gttcgtaccg ttgttaggtt tcccgttatg ctttggcaaa       60
tttccaatag gatcctatgt gcttatcatc gcgggagtac tcattgctat gatcctaact    120
atatttctta tgacttgctg cggtcgaggg aatagaccaa aaagcacaca acactcgctg    180
ggcggaatcg gtcgaaaagt ctcagcaact agtcaatcag gaaaagttat aagctcctgg   240
gaaagccaca gtctggagg tgagactaga ctatga                                276

<210> SEQ ID NO 28
<211> LENGTH: 276
<212> TYPE: DNA
<213> ORGANISM: artificial sequence
<220> FEATURE:
<223> OTHER INFORMATION: degeneratde nucleotide sequence encoding signal
      and membrane-anchoring peptides derived from the rabies
      glycoprotein respectively of ERA and PG strains
      (M38452, v2, ay009097, v2)

<400> SEQUENCE: 28
atggtaccgc aagccctgct attcgtacct ttattggtct ttcccctctg tttcggtaag       60
tttcctatag gatcctacgt actgctatcg gcaggcacgt tgatcgcact aatgcttatc     120
atcttcctaa taacctgctg caagcgggtt gataggcccg aaagtaccca aggtccttg      180

```
agaggtaccg gacgcaacgt atcggtaacg tcgcaaagcg gcaagttcat tagcagttgg    240
gagtcgcaca aatcaggtgg agagaccgc ctgtga                                276
```

SIGNALING PEPTIDES

CROSS-REFERENCE TO PRIORITY/PCT APPLICATIONS

This application is a U.S. National Stage application pursuant to 35 U.S.C. §371 of PCT/EP 2008/051035, filed Jan. 29, 2008, and designating the United States (published in the English language on Nov. 20, 2008, as WO 2008/138649 A2; the title and abstract were also published in English), which claims the priority of European Application No. 07360020.7, filed May 15, 2007, the entire contents of which are incorporated by reference herein.

The present invention relates to novel peptides for use as signal peptides and membrane-anchoring peptides. These peptides are derived from the rabies glycoprotein of various virus strains. The present invention also provides nucleic acid molecules and vectors encoding such peptides, as well as methods using such nucleic acid molecules and vectors for expressing polypeptides of interest destined to be secreted from host cells or anchored to a cell membrane. The invention is particularly relevant in the field of protein expression in various prokaryotic as well as eukaryotic in vitro systems or in an animal or human organism for therapeutic or prophylactic purposes.

Production of recombinant polypeptides has been one of the major challenges within the biotechnological industry during the last two decades. Several plasmid DNA and viral vectors have been generated and employed to express nucleotide sequences in cultured host cells or in living organisms, for a variety of purposes, including vaccination, gene therapy, immunotherapy and production of recombinant polypeptides in cultured cells.

Secretion of polypeptides from recombinantly transformed host cells is generally advantageous since purification steps are facilitated when the recombinant polypeptide can be recovered from the culture supernatant rather from complex mixture of proteins that results when cells are disrupted to release intracellular proteins. Moreover, secretion also reduces the deleterious (e.g. toxic) effect that intracellular expression may have on the host cell or organism. Finally, translocation through the secretory pathway is also required to undergo post-translational modifications and proteolytic cleavage that have roles in stability, folding, immune recognition and biological activity of a particular polypeptide.

For general guidance, secreted polypeptides are expressed as precursors comprising a signal peptide at their N-terminus. Signal peptides are usually constituted by 3 distinct regions: a N-terminal and positively charged region, a central hydrophobic core region, and a C-terminal cleavage site to be recognized by a signal peptidase. The signal peptide ensures effective translocation of the polypeptide precursor across the membrane of the endoplasmic reticulum (ER). The signal peptide is then cleaved off by the signal peptidase during translocation to provide the mature polypeptide (the polypeptide without the signal peptide). Once it has entered the ER, the polypeptide is transported to the Golgi apparatus, and then follows one of a number of routes in the secretory pathway, depending on the nature of the polypeptide and the presence of signaling peptides. For example, the polypeptide may be secreted in the external medium, or routed to cell compartments like the endosomal and lysosomal compartments or anchored to a cell membrane. It is well known in the art that a number of post-translational modifications take place in the ER and Golgi apparatus, such as glycosylation, formation of disulfide bond and proteolytic cleavage of the polypeptide. Improper post-translational modifications typically result in inactive polypeptides and inefficient signal peptidase cleavage in production of heterogeneous polypeptide products, that are unusable especially for human use.

On the other hand, it was previously shown that the immunogenic activity of immunogenic polypeptides could be enhanced by presentation in a form anchored to cell membrane of various subcellular compartments or at the cell surface (Andrew et al., 1990, J. Viol. 64, 4776-4783), likely through improved MHC class I and/or MHC class II-mediated presentation to the host's immune system. For example, Ji et al. (1999, Human Gene Ther. 10:2727-2740) reports that targeting human papillomavirus (HPV)-16 to the endosomal/lysosomal compartment enhances its antitumor activity and permits to increase the generation of tumor cell-specific CD4+ helper T cells and CD8+ cytotoxic T lymphocytes in expressing host organisms. WO99/03885 discloses that targeting HPV-16 E6 and E7 polypeptides at the plasma membrane permits to improve their immunogenic potential and thus their therapeutic efficacy in the host organism. Transport and anchorage of membrane-bound proteins at the cell surface involve signal and membrane-anchoring peptides.

Although a number of such signaling peptides are available in the art, those obtained from the rabies glycoprotein proved to be efficient in particular in the context of vaccinia virus-mediated expression. Therefore, it would be useful to provide additional signaling sequences that ensure efficient translocation through the cell secretion pathway and/or signal peptidase cleavage and/or transport and anchorage to a cell membrane in a large variety of host cells and organisms.

In addition, the nucleotide sequences encoding the rabies glycoprotein-derived signaling peptides object of the present invention have been engineered in order to reduce the percentage of homology between each other to less than 75%, thus permitting their use in multiple gene expression vectors where the expressed polypeptides are to be secreted from the host cell or anchored to a cell membrane, e.g. to the plasma membrane so as to be presented at the cell surface. However, the very limited number of effective signaling peptides, notably signal and membrane-anchoring peptides, has restricted the number of nucleotide sequences that can be expressed from a single vector. Indeed, as known in the art, the use of the same signaling peptides to direct transport and membrane anchorage of each of the polypeptides encoded by a multiple gene expression vector may lead to recombination events between such homologous sequences and loss of the nucleotides comprised between them (Matzke, M., Matzke, A. J. M., Scheid, O. M. In Homologous Recombination and Gene Silencing in Plants; Paszkowski, J. Ed. Kluwer Academic Publishers, Netherlands, 1994; pp 271-300). This instability problem can render the vector stock unusable, especially for human clinical trial.

As detailed above, there is a need in the art for providing alternative signaling peptides for recombinantly producing secreted or membrane-anchored polypeptides, especially in eukaryotic host cells and organisms. The present invention addresses this need in providing novel peptides obtained from the glycoproteins of various rabies virus strains as signal and membrane-anchoring peptides. Such peptides have proved to be highly effective to direct secretion and membrane anchorage of a polypeptide of interest expressed in eukaryotic cells from a vaccinia virus vector. Further, the present invention also provides nucleic acid molecules encoding such peptides which sequences have been engineered so as to exhibit a percentage of homology between each other of less than 75%. The use of such engineered nucleic acid molecules for providing secretion and membrane-anchorage of multiple polypeptides of interest expressed from a single vector significantly reduces the likelihood of homologous recombination events that naturally occur when homologous sequences are present in such a vector construct. Thus, the present invention constitutes an important tool in recombinant technology, especially in the context of multiple gene expression vectors for effecting secretion and membrane presentation of a variety of polypeptides especially in eukaryotic host cells.

This technical problem is solved by the provision of the embodiments as defined in the claims.

Other and further aspects, features and advantages of the present invention will be apparent from the following description of the presently preferred embodiments of the invention. These embodiments are given for the purpose of disclosure.

Accordingly, in a first aspect, the present invention provides a peptide selected from the group consisting of peptides essentially consisting of, or consisting of the amino acid sequences shown in SEQ ID NO: 1, SEQ ID NO: 2, SEQ ID NO: 3, SEQ ID NO: 4 and SEQ ID NO: 5.

As used herein throughout the entire application, the terms "a" and "an" are used in the sense that they mean "at least one", "at least a first", "one or more" or "a plurality" of the referenced compounds or steps, unless the context dictates otherwise.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

As used herein, when used to define products, compositions and methods, the term "comprising" is intended to mean that the products, compositions and methods include the referenced components or steps, but not excluding others. "Consisting essentially of" shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps. For example, a peptide "consists of" an amino acid sequence when the peptide does not contain any amino acids but the recited amino acid sequence. A peptide "consists essentially of" an amino acid sequence when such an amino acid sequence is present together with only a few additional amino acid residues, typically from about 1 to about 10 or so additional residues. A peptide "comprises" an amino acid sequence when the amino acid sequence is at least part of the final amino acid sequence of the peptide. Such a peptide can have a few up to several hundred additional amino acids residues. Such additional amino acid residues may play a role in peptide trafficking, facilitate polypeptide production or purification; prolong half-life, among other things. The same can be applied for nucleotide sequences.

The term "amino acid" as used herein refers to naturally occurring L-amino acids, i.e. the 20 genetic encoded amino acids alanine (Ala or A), valine (Val or V), leucine (Leu or L), isoleucine (Ile or I), proline (Pro or P), methionine (Met or M), phenylalanine (Phe or F), tryptophan (Trp or W), glycine (Gly or G), serine (Ser or S), threonine (Thr or T), cysteine (Cys or C), tyrosine (Tyr or Y), asparagine (Asn or N), glutamine (Gln or Q), aspartic acid (Asp or D), glutamic acid (Glu or E), lysine (Lys or K), arginine (Arg or R), and histidine (His or H), as well as naturally occurring derivatives thereof, such as beta-alanine, ornithine, or methionine sulfoxide or amino acids that are modified on one or more alpha-amino, alpha-carboxyl, or side-chain, e.g., by appendage of a methyl, formyl, acetyl, glycosyl, phosphoryl, and the like.

The terms "polypeptide", "peptide" and "protein" are used herein interchangeably to denote to polymers of amino acid residues which comprise 9 or more amino acids bonded via peptide bonds. The polymer can be linear, branched or cyclic. As a general indication, if the amino acid polymer is long (e.g. more than 80 amino acid residues), it is preferably referred to as a polypeptide or a protein. By way of consequence, a "peptide" refers to a fragment of about 9 to about 80 amino acids, advantageously of about 10 to about 75 amino acids, preferably of about 20 to about 70 amino acids, and more preferably of about 23 to about 66 amino acids in length. A peptide may comprise a selected region of a naturally-occurring (i.e. native) protein such as one involved in polypeptide localisation (e.g. in addressing a polypeptide to a particular cell compartment or membrane). The definition of the term "polypeptide/peptide" encompasses native as well as modified polypeptides/peptides.

The term "native" as used herein refers to a material obtained (e.g. isolated, purified) from a source in nature as distinct from a material artificially modified or altered by man in the laboratory. For example, a native polypeptide/peptide is encoded by a gene that is present in the genome of a wild-type organism or cell. By contrast, a modified polypeptide/peptide is encoded by a nucleic acid molecule that has been modified in the laboratory so as to differ from the native polypeptide/peptide, e.g. by insertion, deletion or substitution of one or more amino acid(s) or any combination of these possibilities. When several modifications are contemplated, they can concern consecutive residues and/or non consecutive residues.

A "signaling peptide" is a peptide that enables a specific localisation of a polypeptide comprising that peptide in a given host cell or organism. Examples of signaling peptides include signal peptides and membrane anchoring peptides.

A "signal peptide" or "signal sequence" as used herein refers to an amino acid sequence which is capable of initiating the passage of a polypeptide to which it is operably linked into the endoplasmic reticulum (ER) of a host cell. The signal peptide is generally cleaved off by an endopeptidase (e.g. a specific ER-located signal peptidase) to release the (mature) polypeptide. The length of a signal peptide is typically in the range from about 10 to about 40 amino acids, advantageously from about 15 to about 30 amino acids and preferably from about 18 to about 25 amino acids, with a special preference for about 23 amino acids including a Met initiator residue.

A "membrane-anchoring peptide" as used herein refers to an amino acid sequence hydrophobic in nature which is capable of anchoring a polypeptide to which it is operably linked to a cell membrane, and especially to the plasma membrane. The length of a membrane-anchoring peptide is typically in the range from about 20 to about 85 amino acids, advantageously from about 25 to about 75 amino acids and preferably from about 30 to about 70 amino acids, with a special preference for about 66 amino acids. Preferably it contains a central highly hydrophobic domain that is capable of spanning the lipid bilayer of the cell membrane one or more time or interacting with outer surface of a membrane.

A "chimeric" polypeptide as used herein refers to a single polypeptide chain comprising polypeptides/peptides in a different position in the sequence than occurs in nature. The various polypeptides/peptides constituting the chimeric polypeptide normally exist in separate proteins in nature and are linked together in the chimeric polypeptide; or they may exist in the same protein in the nature but in a different arrangement than in the chimeric polypeptide. For example, a chimeric polypeptide may be constituted of a signal peptide and a polypeptide of interest that are obtained from different sources. Another chimeric polypeptide may be constituted of a signal peptide, a polypeptide of interest and a membrane-anchoring peptide, wherein the polypeptide of interest is obtained from different sources than the signal peptide and/or membrane-anchoring peptide.

The term "operably linked" refers to a juxtaposition of at least two components, wherein the components so described are in a relationship permitting them to function in the expected manner. For instance a promoter is operably linked to a nucleotide sequence if the promoter initiates and enables its transcription to permit expression in the host cell or organism. A signal peptide is operably linked to a polypeptide if it initiates and enables its translocation through the ER and then cleaved off to release the polypeptide. A membrane-anchoring peptide is operably linked to a polypeptide if it enables its anchorage to a cell membrane, and especially to the plasma membrane.

As used herein, a "vector" may be any agent capable of delivering and expressing nucleic acid molecule(s) in a host cell or organism. A vector may be extrachromosomal (e.g. episome) or integrating (for being incorporated into the host chromosomes), autonomously replicating or not, multi or low copy, double-stranded or single-stranded, naked or complexed with other molecules (e.g. vectors complexed with lipids or polymers to form particulate structures such as liposomes, lipoplexes or nanoparticles, vectors packaged in a viral capsid, and vectors immobilised onto solid phase particles, etc.).

The terms "nucleic acid", "nucleic acid molecule", "polynucleotide" and "nucleotide sequence" are used herein interchangeably and define a nucleotide sequence of any length of either deoxyribonucleic acid (DNA) or ribonucleic acid (RNA) molecules or any combination thereof. The definition encompasses single or double-stranded, linear or circular, naturally-occurring or synthetic nucleotides. Moreover, such nucleotides may comprise non-naturally occurring nucleotides (e.g. methylated nucleotides and nucleotide analogs such as those described in U.S. Pat. No. 5,525,711, U.S. Pat. No. 4,711,955 or EPA 302 175) as well as chemical modifications (e.g. see WO 92/03568; U.S. Pat. No. 5,118,672) in order to increase the in vivo stability of the nucleic acid, enhance the delivery thereof, or reduce the clearance rate from the host subject. If present, modifications may be imparted before or after polymerization of the nucleotides.

As used herein the term "sequence homology" (or sequence identity) is generally expressed as a percentage and denotes nucleotide sequences that retain a given degree of identity each other. The percent homology between two nucleotide sequences is a function of the number of identical positions shared by the sequences, taking into account the number of gaps which need to be introduced for optimal alignment and the length of each gap. Various computer programs and mathematical algorithms are available in the art to determine percentage homology between nucleotide sequences such as GCG Wisconsin package and the Basic Local alignment Search Tool (BLAST) program which is publicly available at National Center for Biotechnology Information (NCBI) and described in printed publications (e.g. Altschul et al., 1990, J. Mol. Biol. 215, 403-410).

The term "host cell" as used herein defines any cell which can be or has been the recipient of the vector of this invention and progeny of such cells. This term should be understood broadly so as to encompass isolated cells, a group of cells, as well as particular organization of cells, e.g. in tissue or organ. Such cells can be primary, transformed or cultured cells.

The term "organism" as used herein refers to a vertebrate, particularly a member of the mammalian species and especially domestic animals, farm animals, sport animals, and primates including humans.

In one embodiment, the present invention provides novel isolated peptides which exhibit the functional properties of a signal peptide as defined above, which essentially consists of or consists of the amino acid sequence shown in SEQ ID NO: 1 (MVPQVLLFVPLLGFPLCFGKFPI) or in SEQ ID NO: 2 (MVPQALLLVPLLGFSLCFGKFPI).

More specifically, the signal peptide shown in SEQ ID NO: 1 derives from the signal peptide present at the N-terminus of the glycoprotein precursor of rabies virus ERA Strain which is disclosed in UniProt database under accession number M38452. For general information, the native ERA strain signal peptide consists of the amino acid sequence of SEQ ID NO: 6 (MVPQALLFVPLLVFPLCFGKFPI) and differs from the signal peptide of SEQ ID NO: 1 in two positions, respectively in position 5 where an Ala residue is present in the native peptide versus a Val residue in the signal peptide of the invention and in position 13 where a Val residue is present in the native peptide versus a glycine in the signal peptide of the invention.

The signal peptide shown in SEQ ID NO: 2 derives from the signal peptide present at the N-terminus of the glycoprotein precursor of rabies virus PG Strain which is disclosed in UniProt database under accession number ay009097. For general information, the native PG strain signal peptide consists of the amino acid sequence of SEQ ID NO: 7 (MVPLALLLVPLLGFSLCFGKFPI) and differs from the signal peptide of SEQ ID NO: 2 in position 4 where a Leu residue is present in the native peptide versus a Gln residue in the signal peptide of the invention.

The peptides of the invention may be modified if necessary provided that modification(s) does/do not alter the signal peptide activity. For example one may delete the initiator Met residue (if the polypeptide to be expressed contains it)

The present invention also provides the use of a peptide essentially consisting of or consisting of the amino acid sequence shown in SEQ ID NO: 1 or SEQ ID NO: 2, as a signal peptide. The peptide of the invention can be independently used in combination with any additional signaling peptide(s), especially a membrane-anchoring peptide as described herein to initiate or enable appropriate transport and anchorage of a polypeptide of interest to a cell membrane.

The present invention also provides novel isolated peptides which exhibit the functional properties of a membrane-anchoring peptide as defined above, which essentially consists of, or consists of the amino acid sequence shown in SEQ ID NO: 3, SEQ ID NO: 4 or SEQ ID NO: 5:

```
                                          (SEQ ID NO: 3)
YVLLSAGTLIALMLIIFLITCCKRVDRPESTQRSLRGTGRNVSVTSQSGK

FISSWESHKSGGETRL;

(SEQ ID NO: 4)
YVLLSAGTLIALMLIIFLMTCCRKVDRPESTQRSLRGTGRNVSVTSQSGK

FISSWESHKSGGETRL;

(SEQ ID NO: 5)
YVLIIAGVLIAMILTIFLMTCCGRGNRPKSTQHSLGGIGRKVSATSQSGK

VISSWESHKSGGETRL.
```

More specifically, the membrane-anchoring peptide shown in SEQ ID NO: 3 derives from the membrane-anchoring peptide present at the C-terminus of the rabies glycoprotein of PG strain which is disclosed in UniProt database under accession number ay009097. For general information, the native PG strain membrane-anchoring peptide consists of the amino acid sequence of SEQ ID NO: 8 (YVLLSAGTLIALMLII-FLITCCKRVDRPESTQRSLRGTGRNVS-VTSQSGKFIHSWE SYKSGGETGL) and differs from the membrane-anchoring peptide of SEQ ID NO: 3 in 3 positions.

The membrane-anchoring peptide shown in SEQ ID NO: 4 derives from the membrane-anchoring peptide present at the C-terminus of the rabies glycoprotein of Nishigahara strain which is disclosed in UniProt database under accession number S72465. For general information, the native Nishigahara strain membrane-anchoring peptide consists of the amino acid sequence of SEQ ID NO: 9 (YVLLSAGTLIALMLII-FLMTCCRKVDRPESTQRSLRGTGRNVS-VTSQSGKFIPSWE SYKSGGETGL) and differs from the membrane-anchoring peptide of SEQ ID NO: 4 in 3 positions.

The membrane-anchoring peptide shown in SEQ ID NO: 5 derives from the membrane-anchoring peptide present at the C-terminus of the rabies glycoprotein of artic fox strain which is disclosed in UniProt database under accession number u11751. For general information, the native artic fox strain membrane-anchoring peptide consists of the amino acid sequence of SEQ ID NO: 10 (YVLIIAGVLIAMILTI-FLMTCCGRGNRPKSTQHSLGGIGRKV-SATSQSGKVISSWE SYKSGGETRL) and differs from the membrane-anchoring peptide of SEQ ID NO: 5 in position 58 where a Tyr residue is present in the native peptide versus a His residue in the membrane-anchoring peptide of the invention.

The peptides of the invention may be modified if necessary provided that modification(s) does/do not alter the membrane-anchoring peptide activity.

The present invention also provides the use of a peptide essentially consisting of or consisting of the amino acid sequence shown in SEQ ID NO: 3, SEQ ID NO: 4 or SEQ ID NO: 5 as a membrane-anchoring peptide. The peptide of the invention can be independently used in combination with one or more additional signaling peptide(s) with a special preference for a signal peptide as described herein so as to enable anchorage of a polypeptide of interest to a cell membrane. Preferably, peptide of the invention permits anchorage of the polypeptide of interest to the plasma membrane such that it can interact with other cell surfaces or with other molecules present in the extracellular medium.

The present invention also provides a chimeric polypeptide comprising a polypeptide of interest and (i) either the peptide of the invention essentially consisting of, or consisting of the amino acid sequence shown in SEQ ID NO: 1 or SEQ ID NO: 2 or (ii) the peptide of the invention essentially consisting of, or consisting of the amino acid sequence shown in SEQ ID NO: 3, SEQ ID NO: 4 or SEQ ID NO: 5 or (iii) both the peptide of the invention essentially consisting of, or consisting of the amino acid sequence shown in SEQ ID NO: 1 or SEQ ID NO: 2 and the peptide of the invention essentially consisting of, or consisting of the amino acid sequence shown in SEQ ID NO: 3, SEQ ID NO: 4 or SEQ ID NO: 5.

A chimeric polypeptide may be generated by chemical synthesis or by genetic means, i.e. by fusing in frame the nucleotide sequences encoding each of the various polypeptides/peptides constituting the chimeric polypeptide. By "fused in frame", it is meant that the expression of the fused nucleotide sequences results in a single polypeptide chain without any translational terminator in between. The fusion can be direct (i.e. the codons encoding each of the polypeptides/peptides are contiguous without any external codon(s) in between) or through a linker (at the junction of two polypeptides/peptides constituting the chimeric polypeptide). The presence of a linker may facilitate correct formation, folding and/or functioning of the chimeric polypeptide or facilitate cloning steps by introducing one or more appropriate restriction sites. For general guidance, linkers are usually 2 to 30 amino acids long and composed of amino acid residues such as glycine, serine, threonine, asparagine, alanine and/or proline. Representative examples of suitable peptide linkers include "Ser-Gly-Ser", "Gly-Ser-Gly", "Ser-Gly", "Gly-Ser" and linkers which nucleotide sequence encodes one or more restriction sites particularly suited for inserting the polypeptide-encoding nucleotide sequence (e.g. the "Gly-Ser" linker which nucleotide sequence "GGATCC" encodes a BamHI restriction site).

In a preferred embodiment, the peptide of the invention essentially consisting of, or consisting of the amino acid sequence shown in SEQ ID NO: 1 or SEQ ID NO: 2 (signal peptide) is linked at the amino terminus of the chimeric polypeptide, i.e. at a location preceding the first residue of the polypeptide of interest (the initiator Met residue is comprised in the signal peptide of the invention).

In one aspect of this embodiment, the chimeric polypeptide of the invention is free of other signaling peptides, in order to provide secretion of the polypeptide of interest from the host cells into the external medium (e.g. the culture medium).

In another and preferred aspect of this embodiment, the chimeric polypeptide of the invention comprises at least one additional signaling peptide, notably a membrane-anchoring peptide in order to enable anchorage of the polypeptide of interest to a cell membrane, and especially to the plasma membrane resulting in its presentation at the cell surface. The membrane-anchoring peptide is preferably linked at the carboxy terminus or within the C-terminal portion of the polypeptide of interest. The carboxy terminus refers to the last amino acid residue of the polypeptide (the residue encoded by the codon preceding the STOP codon) whereas the C-terminal portion refers to the portion comprised in the last third of the polypeptide (assuming that the polypeptide is divided in three portions, the N-terminal, the central and the C-terminal portion, each representing approximately one third of the entire polypeptide). Preferably the C-terminal portion is comprised within the last 100 residues and more preferably within the last 50 residues preceding the carboxy terminus of a given polypeptide. Suitable membrane anchoring peptides for use in this invention can be obtained or isolated from any cellular or viral protein or polypeptide naturally bound to a cell membrane. Such membrane-bound proteins are largely described in the literature publicly available to the skilled person (see for example Branden and Tooze, 1991, in Introduction to Protein Structure p. 202-214, NY Garland). One may cite more particularly the rabies glycoprotein, the HIV virus envelope glycoprotein and the measles virus F protein.

Preferably, the membrane-anchoring peptide comprised in the chimeric polypeptide of the invention is the membrane-anchoring peptide of the invention essentially consisting of, or consisting of the amino acid sequence as shown in any of SEQ ID NO: 3, 4 or 5. More preferably, the chimeric polypeptide of the invention comprises the signal peptide consisting of the amino acid sequence shown in SEQ ID NO: 2, and the membrane-anchoring peptide consisting of the amino acid sequence shown in SEQ ID NO: 3. Alternatively, the chimeric polypeptide of the invention comprises the signal peptide consisting of the amino acid sequence as shown in SEQ ID NO: 1, and the membrane-anchoring peptide consisting of the amino acid sequence shown in SEQ ID NO: 5.

As the signal and membrane-anchoring peptides described herein are derived from rabies glycoproteins, the polypeptide of interest included in the chimeric polypeptide of the invention is preferably heterologous to a rabies virus. A polypeptide "heterologous to a rabies virus" as used herein refers to a polypeptide which is not naturally associated to a wild-type rabies virus or encoded by the genome of wild-type rabies virus.

Suitable polypeptides of interest include for example polypeptides that have commercial or research value as well as polypeptides capable of providing a therapeutic or protective activity in a host organism exhibiting or susceptible to exhibit a disease or disorder. For instance, the polypeptide of interest can be selected from the group consisting of hormones, cytokines, immunogens, receptors, chaperones, immunoglobulins, enzymes, growth factors, fluorescent proteins such as GFP, transporter proteins such as flavodoxins, globins, and metallothioneins, toxins, suicide gene products, structural proteins, and inhibitors such as protease inhibitors. In the context of the present invention, the polypeptide of interest is preferably selected from the group consisting of immunogenic polypeptides and anti-tumor polypeptides.

An "immunogenic" polypeptide refers to a polypeptide able to induce, stimulate, develop or boost an immune system in a host organism into which it is expressed. Such immune response can be humoral or cellular or both humoral and cellular. Humoral response elicits antibody production against the polypeptide in question whereas cellular response elicits T-helper cell and/or CTL response and/or stimulation of cytokine production. Typically, the immunogenic property of a polypeptide can be evaluated either in vitro or in vivo by a variety of assays which are standard in the art (for a general description of techniques available to evaluate the onset and activation of an immune response, see for example the latest edition of Coligan et al., Current Protocols in Immunology; ed J Wiley & Sons Inc, National Institute of Health). For example, detection can be colorimetric, fluorometric or radioactive and suitable techniques include ELISA, Western Blot, radioimmunoassays and immunoprecipitation assays. Measurement of cellular immunity can be performed by measurement of cytokine profiles secreted by activated effector cells including those derived from CD4+ and CD8+ T-cells (e.g. quantification IFNg-producing cells by ELIspot), by determination of the activation status of immune effector cells (e.g. T cell proliferation assays by a classical [$^3$H] thymidine uptake), by assaying for antigen-specific T lymphocytes in a sensitized subject (e.g. peptide-specific lysis in a cytotoxicity assay). The immunogenic property of a polypeptide could also be evaluated in suitable animal models by ELIspot, tetramer-based analytical techniques or other standard techniques for analysis T cell-mediated immunity. Suitable immunogenic polypeptides can be obtained from hepatitis B virus (HBV) (e.g. S, preS2 or preS1-polypeptide as described in EP 414 374; EP 304 578 or EP 198 474); hepatitis C virus (HCV) (e.g. Core (C), the envelop glycoprotein E1, E2, the non-structural polypeptide NS2, NS3, NS4, or NS5 or any combination thereof); human immunodeficiency virus (HIV) (e.g. gp120 or gp160), and papillomavirus.

The papillomavirus immunogenic polypeptide(s) comprised in the chimeric polypeptide of the invention can be an early, a late or any combination thereof. Early papillomavirus polypeptides include E1, E2, E4, E5, E6 and E7 whereas late polypeptides can be L1 or L2. It is preferably obtained from a papillomavirus selected from the group consisting of HPV-16, HPV-18, HPV-30, HPV-31, HPV-33, HPV-35, HPV-39, HPV-45, HPV-51, HPV-52, HPV-56, HPV-58, HPV-59, HPV-66, HPV-68, HPV-70 and HPV-85. The nucleotide sequences of a number of papillomavirus genomes and the amino acid sequences of the encoded polypeptides have been described in the literature and are available in specialized data banks. For general information, HPV-16 genome is described in Genbank under accession numbers NC_01526 and K02718; HPV-18 under NC_001357 and X05015; HPV-31 under J04353; HPV-33 under M12732; HPV-35 under NC_001529; HPV-39 under NC_001535; HPV-45 under X74479; HPV-51 under NC_001533; HPV-52 under NC_001592; HPV-56 under X74483; HPV-58 under D90400; HPV-59 under NC_001635; HPV-68 under X67160 and M73258; HPV-70 under U21941; and HPV-85 under AF131950. However, the present invention is not limited to these exemplary sequences. Indeed, the natural genetic variation observed between different papillomavirus isolates is included within the scope of the invention as well as non-natural modification(s) such as those described in the literature available to the skilled person (see for example Yasugi et al. 1997, J. Virol 71, 5942-51 describing modified E1 polypeptides; Sakai et al., 1996, J. Virol. 70, 1602-1611 describing modified E2 polypeptides and WO99/03885 describing modified E6 and E7 polypeptides suitable for use in this invention).

An "anti-tumor" polypeptide refers to a polypeptide able to provide suppression or a net reduction in the expansion of tumor cells. The antitumor property of a polypeptide can be determined in appropriate animal models or in the treated subject by a decrease of the actual tumor size over a period of time. A variety of methods may be used to estimate tumor size including radiologic methods (e.g., single photon and positron emission computerized tomography; see generally, "Nuclear Medicine in Clinical Oncology," Winkler, C. (ed.) Springer-Verlag, New York, 1986), methods employing conventional imaging reagents (e.g., Gallium-67 citrate), immunologic methods (e.g., radiolabeled monoclonal antibody directed to specific tumor markers) as well as ultrasound methods (see, "Ultrasonic Differential Diagnosis of Tumors", Kossoff and Fukuda, (eds.), Igaku-Shoin, New York, 1984). Alternatively, the anti-tumor property of a polypeptide may be determined based upon a decrease in the presence of a tumor marker. Examples include PSA for the detection of prostate cancer and CEA for the detection of colorectal and certain breast cancers. Further, the anti-tumor property of a polypeptide can be determined in a suitable animal model, e.g. using mice injected with a representative human cancer cell line. After palpable tumors have developed, the mice are injected with the vector of the invention, and then monitored for reduced tumor growth rate and increased survival. In addition, a variety of in vitro methods can be used to predict in vivo tumor inhibition. Suitable antitumor polypeptides include tumour-associated antigens (TAAs) such as MUC-1 (WO92/07000; Acres et al., 2005, Exp. Rev. Vaccines 4(4)), BRCA-1, BRCA-2 (Palma et al., 2006, Critical Reviews in Oncology/haematology 27, 1-23), Carcinoembryonic antigen CEA (Conroy et al., 1995, Gene Ther; 2, 59-65), MAGE (WO99/40188; De Plaen et al., 1994, Immunogenetics 40, 360-369), MART-1, gp 100 (Bakker et al., 1994, J. Exp. Med. 179, 1005-9), PRAME, BAGE, Lage (also known as NY Eos 1) SAGE, HAGE (WO99/53061), GAGE (Robbins and Kawakami, 1996. Current Opinions in Immunol. 8, 628-36) and Prostate specific antigen (PSA) (Ferguson, et al., 1999, Proc. Natl. Acad. Sci. USA. 96, 3114-9; WO98/12302, WO98/20117 and WO00/04149) as well as viral polypeptides from viruses having tumor-inducing potential.

The present invention also provides an isolated nucleic acid molecule comprising, essentially consisting of or consisting of at least a nucleotide sequence encoding the peptide of the invention or the chimeric polypeptide of the invention.

In a preferred embodiment, the present invention provides an isolated nucleic acid molecule comprising at least one of the nucleotide sequences shown in any of SEQ ID NO: 11-28.

More specifically, the nucleotide sequences of SEQ ID NO: 11, SEQ ID NO: 14 and SEQ ID NO: 15 encode a signal peptide having the amino acid sequence of SEQ ID NO: 1, the nucleotide sequence of SEQ ID NO: 12 encodes a signal peptide having the amino acid sequence of SEQ ID NO: 2, the nucleotide sequence of SEQ ID NO: 13 encodes the signal peptide present in the rabies glycoprotein of Nishigahara strain (disclosed in UniProt under accession number S72465) and the nucleotide sequence of SEQ ID NO: 16 encodes the signal peptide present in the rabies glycoprotein of ERA strain (disclosed in UniProt under accession number M38452).

The nucleotide sequences shown in SEQ ID NO: 17 and SEQ ID NO: 22 encode the native membrane-anchoring peptide present in the rabies glycoprotein of PG strain (disclosed in UniProt under accession number ay009097); the nucleotide sequence shown in SEQ ID NO: 18 encodes a membrane-anchoring peptide having the amino acid sequence of SEQ ID NO: 3; the nucleotide sequence shown in SEQ ID NO: 19 encodes a membrane-anchoring peptide having the amino acid sequence of SEQ ID NO: 4; the nucleotide sequences shown in SEQ ID NO: 20 and 21 encode a membrane-anchoring peptide having the amino acid sequence of SEQ ID NO: 5.

The nucleotide sequence of SEQ ID NO: 23 (M38452, v1) comprises the nucleotide sequence disclosed in SEQ ID NO: 11 linked to the nucleotide sequence of SEQ ID NO: 17 through a BamHI linker; the nucleotide sequence of SEQ ID NO: 24 comprises the nucleotide sequence disclosed in SEQ ID NO: 12 linked to the nucleotide sequence of SEQ ID NO: 18 through a BamHI linker; the nucleotide sequence of SEQ ID NO: 25 comprises the nucleotide sequence disclosed in SEQ ID NO: 13 linked to the nucleotide sequences of SEQ ID NO: 19 through a BamHI linker; the nucleotide sequence of SEQ ID NO: 26 comprises the nucleotide sequence disclosed in SEQ ID NO: 14 linked to the nucleotide sequence of SEQ ID NO: 20 through a BamHI linker; the nucleotide sequence of SEQ ID NO: 27 comprises the nucleotide sequence disclosed in SEQ ID NO: 15 linked to the nucleotide sequences of SEQ ID NO: 21 through a BamHI linker; and the nucleotide sequence of SEQ ID NO: 28 comprises the nucleotide sequence disclosed in SEQ ID NO: 16 linked to the nucleotide sequences of SEQ ID NO: 22 through a BamHI linker.

Moreover, the nucleotide sequences of SEQ ID NO: 23-28 have been engineered so as to reduce the percentage of homology between each other to less than 75% as illustrated in the appended example section, thus permitting the combined use of at least two of them in a multiple gene expression vector to enable secretion and/or membrane anchorage of multiple polypeptides of interest. The combined use of the nucleotide sequences of the invention is advantageous when multiple polypeptides need to be expressed from a single vector and secreted and/or transported to the cell membrane. The use of the nucleotide sequences of the present invention permits to reduce the risk of homologous recombination events that are likely to occur when homologous sequences are present in the same vector. It is well known in the art that the native rabies signaling sequences exhibit a high degree of homology between them and such homology impedes their combined use which may negatively influence the vector stability and result in vector stocks improper for human use.

Reduction of the percentage of homology between two nucleic acid molecules of the invention is typically achieved by modifying the codon usage pattern. As a starting point, a sequence alignment between the nucleic acid molecules before modification may be used in order to reveal the homologous portions thereof. Then the degeneracy of the genetic code is used to reduce the percentage of homology in such homologous portion to less than 75%. Whereas methionine and tryptophane residues are each encoded by a unique nucleic acid triplet (i.e. codon), different codons can be used to encode the 18 other amino acids (degeneracy of the genetic code). Modification of the codon usage pattern is typically performed by replacing one or more "native" codon(s) with another codon(s). For example, the replacement of the Arg-encoding AGA codon with the Arg-encoding CGC codon will reduce homology in 2 of 3 positions of the codon. It is not necessary to degenerate all native codons since homology can be sufficiently reduced with partial replacement.

Moreover, the disclosed nucleotide sequence may be further modified by the skilled person. For example, the first codon encoding the initiator Met residues present at the N-terminus of the signal peptide and/or the last codon encoding a TGA STOP codon present at the C-terminus of the membrane-anchoring peptide may be deleted, if the polypeptide of interest is equipped with such regulatory codons. Further it is also possible to substitute the BamHI linker present at the junction of the signal and membrane-anchoring sequences by another linker containing the restriction site(s) more appropriate for cloning the polypeptide-encoding nucleotide sequence.

In a preferred embodiment, the nucleotide sequence encoding the polypeptide of interest is comprised in the nucleic acid molecule of the invention at the junction between the nucleotide sequence encoding the signal peptide (defined in SEQ ID NO: 11-16) and the nucleotide sequence encoding the membrane-anchoring peptide (defined in SEQ ID NO: 17-22). More preferably, it is inserted between approximately position 70 and approximately position 76 of SEQ ID NO: 23-28 in the BamHI linker.

In another preferred embodiment, the nucleic acid molecule of the invention is placed under the control of appropriate regulatory elements in order to ensure its expression in a given host cell or organism. As used herein, the term "regulatory sequences" refers to any sequence that allows, contributes or modulates the expression of a nucleic acid molecule in a given host cell, including replication, duplication, transcription, splicing, translation, stability and/or transport of the nucleic acid or one of its derivative (i.e. mRNA) into the host cell. Such regulatory sequences are well known in the art (see for example Goeddel, 1990, Gene Expression Technology: Methods in Enzymology 185, Academic Press, San Diego). It will be appreciated by those skilled in the art that the choice of the regulatory sequences can depend on factors such as the vector type, the host cell, the level of expression desired, etc.

The promoter is of special importance and the present invention encompasses the use of constitutive promoters which direct expression of the nucleic acid molecule in many types of host cells and those which direct expression only in certain host cells (e.g., tissue-specific regulatory sequences) or in response to specific events or exogenous factors (e.g. by temperature, nutrient additive, hormone or other ligand). Suitable promoters for constitutive expression in eukaryotic systems include viral promoters, such as SV40 promoter, the cytomegalovirus (CMV) immediate early promoter or enhancer (Boshart et al., 1985, Cell 41, 521-530), the adenovirus early and late promoters, the thymidine kinase (TK)

promoter of herpes simplex virus (HSV)-1 and retroviral long-terminal repeats (e.g. MoMuLV and Rous sarcoma virus (RSV) LTRs) as well as cellular promoters such as the phosphoglycero kinase (PGK) promoter (Hitzeman et al., 1983, Science 219, 620-625; Adra et al., 1987, Gene 60, 65-74). Suitable promoters useful to drive expression of the nucleic acid molecule in a poxviral vector include the 7.5K, H5R, TK, p28, p11 or K1L promoters of vaccinia virus. Alternatively, one may use a synthetic promoter such as those described in Chakrabarti et al. (1997, Biotechniques 23, 1094-1097), Hammond et al. (1997, J. Virological Methods 66, 135-138) and Kumar and Boyle (1990, Virology 179, 151-158) as well as chimeric promoters between early and late poxviral promoters.

Inducible promoters are regulated by exogenously supplied compounds, and include, without limitation, the zinc-inducible metallothionein (MT) promoter (Mc Ivor et al., 1987, Mol. Cell Biol. 7, 838-848), the dexamethasone (Dex)-inducible mouse mammary tumor virus (MMTV) promoter, the T7 polymerase promoter system (WO 98/10088), the ecdysone insect promoter (No et al., 1996, Proc. Natl. Acad. Sci. USA 93, 3346-3351), the tetracycline-repressible promoter (Gossen et al., 1992, Proc. Natl. Acad. Sci. USA 89, 5547-5551), the tetracycline-inducible promoter (Kim et al., 1995, J. Virol. 69, 2565-2573), the RU486-inducible promoter (Wang et al., 1997, Nat. Biotech. 15, 239-243 and Wang et al., 1997, Gene Ther. 4, 432-441), the rapamycin-inducible promoter (Magari et al., 1997, J. Clin. Invest. 100, 2865-2872) and the lac, TRP, and TAC promoters from *E. coli*.

The regulatory sequences in use in the context of the present invention can also be tissue-specific to drive expression of the nucleic acid molecule in specific tissues where therapeutic benefit is desired. Suitable promoters can be taken from genes that are preferentially expressed in tumor cells. Such genes can be identified for example by display and comparative genomic hybridization (see for example U.S. Pat. Nos. 5,759,776 and 5,776,683).

Those skilled in the art will appreciate that the regulatory elements controlling the expression of the nucleic acid molecule may further comprise additional elements for proper initiation, regulation and/or termination of transcription (e.g. polyA transcription termination sequences), mRNA transport (e.g. nuclear localization signal sequences), processing (e.g. splicing signals), stability (e.g. introns and non-coding 5' and 3' sequences), and translation (e.g. tripartite leader sequences, ribosome binding sites, Shine-Dalgarno sequences, etc.) into the host cell or organism.

The present invention also provides a vector for expressing one or more chimeric polypeptide(s) of the invention. Advantageously, the vector of the invention comprises one or more nucleic acid molecule as described herein, with a special preference for 2, 3 or even 4 nucleic acid molecules. Desirably, each of the nucleic acid molecules inserted in the vector of the invention differs at least by the signal peptide, membrane anchoring peptide and/or polypeptide of interest which it encodes. Preferably, the vector of the invention comprises 2, 3, 4 or even more signal and membrane-anchoring peptide-encoding nucleotide sequences exhibiting a percentage of homology between each other of less than 75% (e.g. selected from the group consisting of SEQ ID NO: 23-28). More preferably the vector of the invention comprises the nucleotide sequence of SEQ ID NO: 24 to enable expression of a first polypeptide of interest to the cell membrane and the nucleotide sequence of SEQ ID NO: 28 to enable expression of a second polypeptide of interest to the cell membrane.

A variety of vector systems may be used to express the chimeric polypeptide of the invention, including bacteriophage, plasmid or cosmid vectors suitable for prokaryotic cells (e.g. *E. coli* or *Bacillus subtilis*); yeast expression vectors suitable for yeast host cells (e.g. *Saccharomyces cerevisiae, Saccharomyces pombe, Pichia pastoris*); virus expression vectors (e.g. baculovirus) suitable for insect host cells (e.g. Sf 9 cells); virus expression vectors (e.g. cauliflower mosaic virus CaMV; tobacco mosaic virus TMV) or plasmid vectors (e.g. Ti plasmid) suitable for plant cells; or plasmid or viral vectors suitable for high eukaryotic host cells or organisms.

Suitable vectors for use in prokaryotic systems include without limitation pBR322 (Gibco BRL), pUC (Gibco BRL), pBluescript (Stratagene), p Poly (Lathe et al., 1987, Gene 57, 193-201), pTrc (Amann et al., 1988, Gene 69, 301-315); pET 11d (Studier et al., 1990, Gene Expression Technology: Methods in Enzymology 185, 60-89); pIN (Inouye et al., 1985, Nucleic Acids Res. 13, 3101-3109; Van Heeke et al., 1989, J. Biol. Chem. 264, 5503-5509); and pGEX vectors where the nucleic acid molecule of the invention can be expressed in fusion with glutathione S-transferase (GST).

Suitable vectors for expression in yeast (e.g. *S. cerevisiae*) include, but are not limited to pYepSec1 (Baldari et al., 1987, EMBO J. 6, 229-234), pMFa (Kujan et al., 1982, Cell 30, 933-943), pJRY88 (Schultz et al., 1987, Gene 54, 113-123), pYES2 (Invitrogen Corporation, San Diego, Calif.) and pTEF-MF (Dualsystems Biotech Product code: P03303).

The vectors suited for expression in eukaryotic host cells or organisms can be of viral or non viral (e.g. plasmid DNA). Suitable plasmid vectors include, without limitation, pREP4, pCEP4 (Invitrogene), pCI (Promega), pCDM8 (Seed, 1987, Nature 329, 840) and pMT2PC (Kaufman et al., 1987, EMBO J. 6, 187-195), pVAX and pgWiz (Gene Therapy System Inc; Himoudi et al., 2002, J. Virol. 76, 12735-12746). A "viral vector" is used herein according to its art-recognized meaning. It refers to any vector that comprises at least one element of viral origin, including a complete viral genome, a portion thereof or a modified viral genome as described below as well as viral particles generated thereof (e.g. viral vector packaged into a viral capsid to produce infectious viral particles). Viral vectors of the invention can be replication-competent, or can be genetically disabled so as to be replication-defective or replication-impaired. The term "replication-competent" as used herein encompasses replication-selective and conditionally-replicative viral vectors which are engineered to replicate better or selectively in specific host cells (e.g. tumoral cells). Viral vectors may be obtained from a variety of different viruses, and especially from a virus selected from the group consisting of retrovirus, adenovirus, adeno-associated virus (AAV), poxvirus, herpes virus, measle virus and foamy virus.

In one embodiment, the vector of the invention is an adenoviral vector (for a review, see "Adenoviral vectors for gene therapy", 2002, Ed D. Curiel and J. Douglas, Academic Press). It can be derived from any human or animal adenovirus. Any serotype and subgroup can be employed in the context of the invention. One may cite more particularly subgroup A (e.g. serotypes 12, 18, and 31), subgroup B (e.g. serotypes 3, 7, 11, 14, 16, 21, 34, and 35), subgroup C (e.g. serotypes 1, 2, 5, and 6), subgroup D (e.g. serotypes 8, 9, 10, 13, 15, 17, 19, 20, 22-30, 32, 33, 36-39, and 42-47), subgroup E (serotype 4), and subgroup F (serotypes 40 and 41). Particularly preferred are human adenoviruses 2 (Ad2), 5 (Ad5), 6 (Ad6), 11 (Ad11), 24 (Ad24) and 35 (Ad35). Such adenovirus are available from the American Type Culture Collection (ATCC, Rockville, Md.) and have been the subject of numerous publications describing their sequence, organization and methods of producing, allowing the artisan to apply them (see for example U.S. Pat. No. 6,133,028; U.S. Pat. No. 6,110,735; WO 02/40665; WO 00/50573; EP 1016711; Vogels et al., 2003, J. Virol. 77, 8263-8271).

The adenoviral vector of the present invention can be replication-competent. Numerous examples of replication-competent adenoviral vectors are readily available to those skilled in the art (see for example Hernandez-Alcoceba et al., 2000, Human Gene Ther. 11, 2009-2024; Nemunaitis et al., 2001, Gene Ther. 8, 746-759; Alemany et al., 2000, Nature Biotechnology 18, 723-727; WO00/24408; U.S. Pat. No. 5,998,205, WO99/25860, U.S. Pat. No. 5,698,443, WO00/46355, WO00/15820 and WO01/36650).

Alternatively, the adenoviral vector of the invention can be replication-defective (see for example WO94/28152). Preferred replication-defective adenoviral vectors are E1-defective (e.g. U.S. Pat. No. 6,136,594 and U.S. Pat. No. 6,013,638), with an E1 deletion extending from approximately positions 459 to 3328 or from approximately positions 459 to 3510 (by reference to the sequence of the human adenovirus type 5 disclosed in the GeneBank under the accession number M 73260 and in Chroboczek et al., 1992, Virol. 186, 280-285). The cloning capacity and safety can further be improved by deleting additional portion(s) of the adenoviral genome (e.g. in the non essential E3 region or in other essential E2, E4 regions as described in Lusky et al., 1998, J. Virol 72, 2022-2032).

The nucleic acid molecule(s) of the invention can be inserted in any location of the adenoviral vector, as described in Chartier et al. (1996, J. Virol. 70, 4805-4810) and positioned in sense and/or antisense orientation relative to the natural transcriptional direction of the region of insertion. For example, it can be inserted in replacement of the E1 region or alternatively in replacement of the E3 region.

In another embodiment, the vector of the invention is a poxviral vector (see for example Cox et al. in "Viruses in Human Gene Therapy" Ed J. M. Hos, Carolina Academic Press). It may be obtained from any member of the poxviridae, in particular canarypox (e.g. ALVAC as described in WO95/27780), fowlpox (e.g. TROVAC as described in Paoletti et al., 1995, Dev. Biol. Stand. 84, 159-163) or vaccinia virus, the latter being preferred. A suitable vaccinia virus can be selected from the group consisting of the Copenhagen strain (Goebel et al., 1990, Virol. 179, 247-266 and 517-563; Johnson et al., 1993, Virol. 196, 381-401), the Wyeth strain, NYVAC (see WO92/15672 and Tartaglia et al., 1992, Virology 188, 217-232) and the highly attenuated modified Ankara (MVA) strain (Mayr et al., 1975, Infection 3, 6-16). Such vectors and methods of producing are described in numerous documents accessible to the man skilled in the art (e.g. Paul et al., 2002, Cancer gene Ther. 9, 470-477; Piccini et al., 1987, Methods of Enzymology 153, 545-563; U.S. Pat. No. 4,769,330; U.S. Pat. No. 4,772,848; U.S. Pat. No. 4,603,112; U.S. Pat. No. 5,100,587 and U.S. Pat. No. 5,179,993). The nucleic acid molecule(s) of the invention is preferably inserted in a nonessential locus of the poxviral genome, in order that the recombinant poxvirus remains viable and infectious. Nonessential regions are non-coding intergenic regions or any gene for which inactivation or deletion does not significantly impair viral growth, replication or infection. One may also envisage insertion in an essential viral locus provided that the defective function is supplied in trans during production of viral particles, for example by using an helper cell line carrying the complementing sequences corresponding to those deleted in the poxviral genome.

When using the Copenhagen vaccinia virus, the nucleic acid molecule(s) is preferably inserted in the thymidine kinase gene (tk) (Hruby et al., 1983, Proc. Natl. Acad. Sci. USA 80, 3411-3415; Weir et al., 1983, J. Virol. 46, 530-537). However, other insertion sites are also appropriate, e.g. in the hemagglutinin gene (Guo et al., 1989, J. Virol. 63, 4189-4198), in the K1L locus, in the u gene (Zhou et al., 1990, J. Gen. Virol. 71, 2185-2190) or at the left end of the vaccinia virus genome where a variety of spontaneous or engineered deletions have been reported in the literature (Altenburger et al., 1989, Archives Virol. 105, 15-27; Moss et al. 1981, J. Virol. 40, 387-395; Panicali et al., 1981, J. Virol. 37, 1000-1010; Perkus et al, 1989, J. Virol. 63, 3829-3836; Perkus et al, 1990, Virol. 179, 276-286; Perkus et al, 1991, Virol. 180, 406-410).

When using MVA, the nucleic acid molecule(s) can be inserted in anyone of the identified deletions I to VII which occurred in the MVA genome (Antoine et al., 1998, Virology 244, 365-396) as well as in the D4R locus, but insertion in deletion II and/or III is preferred (Meyer et al., 1991, J. Gen. Virol. 72, 1031-1038; Sutter et al., 1994, Vaccine 12, 1032-1040).

When using fowlpox virus, although insertion within the thymidine kinase gene may be considered, the nucleic acid molecule(s) is preferably introduced in the intergenic region situated between ORFs 7 and 9 (see for example EP 314 569 and U.S. Pat. No. 5,180,675).

Moreover, the vector of the invention may also comprise one or more additional element(s) enabling maintenance, propagation or expression of the nucleic acid molecule in a given host cell or organism. Such additional elements include without limitation marker gene(s) in order to facilitate identification and isolation of the recombinant host cells (e.g. by complementation of a cell auxotrophy or by antibiotic resistance), stabilising elements (e.g. cer sequence as described in Summers and Sherrat, 1984, Cell 36, 1097-1103 and DAP system as described in U.S. Pat. No. 5,198,343), and integrative elements (e.g. LTR viral sequences and transposons).

The present invention also provides infectious viral particles comprising the above-described nucleic acid molecules or vectors. No attempts to describe in detail the various methods known for the production of infectious viral particles will be made here. Typically, such viral particles are produced by a process comprising the steps of (a) introducing the viral vector in an appropriate cell line, (b) culturing the cell line under suitable conditions so as to allow the production of said infectious viral particle, recovering the produced infectious viral particle from the culture of said cell line, and optionally purifying said recovered infectious viral particle.

When the viral vector is defective, the infectious particles are usually produced in a complementation cell line which supplies in trans the non functional viral genes. For example, suitable cell lines for complementing E1-deleted adenoviral vectors include the 293 cells (Graham et al., 1997, J. Gen. Virol. 36, 59-72), the PER-C6 cells (Fallaux et al., 1998, Human Gene Ther. 9, 1909-1917) and the HER96 cells. Cells appropriate for propagating poxvirus vectors are avian cells, and most preferably primary chicken embryo fibroblasts (CEF) prepared from chicken embryos obtained from fertilized eggs. The producer cells can be cultured in conventional fermentation bioreactors, flasks and Petri plates under appropriate temperature, pH and oxygen content conditions. The infectious viral particles may be recovered from the culture supernatant or from the cells after lysis. They can be further purified according to standard techniques (chromatography, ultracentrifugation as described for example in WO96/27677, WO98/00524, WO98/22588, WO98/26048, WO00/40702, EP1016700 and WO00/50573).

The present invention also encompasses viral vectors that have been modified to allow preferential targeting to a particular host cell. A characteristic feature of targeted vectors is the presence at their surface of a ligand capable of recognizing and binding to a cellular and surface-exposed component such as a cell-specific marker (e.g. an HPV-infected cell), a tissue-specific marker or a tumor-specific marker. The ligand can be genetically inserted into a polypeptide present on the surface of the vector (e.g. adenoviral fiber, penton, pIX as described in WO94/10323 and WO02/96939 or vaccinia p14 gene product as described in EP 1 146 125).

The invention also relates to host cells comprising the above-described nucleic acid molecules, vectors or infectious viral particles.

Host cells in the context of the invention include prokaryotic cells (e.g. *Escherichia coli, Bacillus, Listeria*), lower eukaryotic cells such as yeast (e.g. *Saccharomyces cerevisiae, Saccharomyces pombe* or *Pichia pastoris*), and other eukaryotic cells such as insect cells, plant and higher eukaryotic cells, with a special preference for mammalian cells (e.g. human or non-human cells). Representative examples of suitable host cells include but are not limited to BHK (baby hamster kidney) cells, MDCK cells (Madin-Darby canine kidney cell line), CRFK cells (Crandell feline kidney cell line), CV-1 cells (African monkey kidney cell line), COS (e.g., COS-7) cells, Chinese hamster ovary (CHO) cells, mouse NIH/3T3 cells, HeLa cells and Vero cells. The term "host cell" also encompasses complementing cells capable of complementing at least one defective function of a replication-defective vector of the invention (e.g. adenoviral vector) such as those cited above.

Methods for introducing a nucleic acid molecule, vector or infectious particle in an isolated host cell are routine in the art and include, e.g microinjection (Capechi et al., 1980, Cell 22, 479-488), CaPO$_4$-mediated transfection (Chen and Okayama, 1987, Mol. Cell Biol. 7, 2745-2752), DEAE-dextran-mediated transfection, electroporation (Chu et al., 1987, Nucleic Acid Res. 15, 1311-1326), lipofection/liposome fusion (Felgner et al., 1987, Proc. Natl. Acad. Sci. USA 84, 7413-7417), particle bombardement (Yang et al., 1990, Proc. Natl. Acad. Sci. USA 87, 9568-9572), gene guns, transduction, viral infection as well as direct administration into a host organism via various means.

Host cells can be used for producing by recombinant means the polypeptide(s) of interest encoded by the nucleic acid molecule(s), vector or infectious particles of the invention. Such techniques are well known in the art (see for example Ausubel, Current Protocols in Molecular Biology, John Wiley, 1987-2002; and the latest edition of Sambrook et al., Molecular Cloning, A Laboratory Manual, Cold Spring Harbor Laboratory Press).

In another embodiment of this invention, the above-described chimeric polypeptide, nucleic acid molecule, vector, infectious viral particle, or host cell (also referred herein to the "active agent") or any combination thereof is comprised in a composition. Advantageously, the composition is a pharmaceutical composition which comprises a therapeutically effective amount of the active agent(s) and a pharmaceutically acceptable vehicle. As used herein a "therapeutically effective amount" is a dose sufficient for the alleviation of one or more symptoms normally associated with the disease or condition desired to be treated or prevented in a host organism. When prophylactic use is concerned, this term means a dose sufficient to prevent or to delay the establishment of a disease or condition in a host organism. For example, a therapeutically effective amount could be that amount that is sufficient to induce or enhance an immune response in the treated organism, or that amount that is sufficient to palliate, ameliorate, stabilize, reverse, slow or delay the progression of the disease (e.g. for instance size reduction or regression of a lesion or a tumor, reversion of a viral infection).

As used herein, a "pharmaceutically acceptable vehicle" is intended to include any and all carriers, solvents, diluents, excipients, adjuvants, dispersion media, coatings, antibacterial and antifungal agents, and absorption delaying agents, and the like, compatible with pharmaceutical administration. Desirably, the composition of the invention comprises one or more carrier and/or diluent non-toxic at the dosage and concentration employed. Such carrier and/or diluent are preferably selected from those usually employed to formulate compositions in either unit dosage or multi-dose form for systemic or mucosal administration. A suitable carrier can be a solvent, a dispersing medium containing, for example, water, ethanol, polyol (for example, glycerol, propylene glycol, liquid polyethylene glycol, and the like), a vegetable oil or suitable mixtures thereof. The diluent is preferably isotonic, hypotonic or weakly hypertonic and has a relatively low ionic strength. Representative examples of suitable diluents include sterile water, physiological saline (e.g. sodium chloride), Ringer's solution, glucose, trehalose or saccharose solutions, Hank's solution, and other aqueous physiologically balanced salt solutions (see for example the most current edition of Remington: The Science and Practice of Pharmacy, A. Gennaro, Lippincott, Williams&Wilkins). The pH of the composition of the invention is suitably adjusted and buffered in order to be appropriate for use in humans or animals, preferably at a physiological or slightly basic pH (between about pH 7.5 to about pH 9, with a special preference for pH 8-8.5). Suitable buffers include phosphate buffer (e.g. PBS), bicarbonate buffer and/or Tris buffer. A particularly preferred composition (especially when the active agent is an adenoviral vector) is formulated in 1M saccharose, 150 mM NaCl, 1 mM MgCl$_2$, 54 mg/l Tween 80, 10 mM Tris pH 8.5. Another preferred composition is formulated in 10 mg/ml mannitol, 1 mg/ml HSA, 20 mM Tris, pH 7.2, and 150 mM NaCl. Such formulations are particularly suited for preserving stability of the composition of the invention over a period of at least two months at either freezing (e.g. −70° C., −40° C., −20° C.), or refrigerated (e.g. 4° C.) temperature.

The composition may also contain one or more pharmaceutically acceptable excipients for providing desirable pharmaceutical or pharmacodynamic properties, including for example modifying or maintaining the pH, osmolarity, viscosity, clarity, colour, sterility, stability, rate of dissolution of the formulation, modifying or maintaining release or absorption into an the human or animal subject.

In addition, the composition of the invention may comprise one or more adjuvant(s) suitable for systemic or mucosal administration in humans. By "adjuvant" it is meant a compound having the ability to enhance the immune response to a particular antigen. The adjuvant can be delivered at or near the site of antigen. Enhancement of humoral immunity is typically manifested by a significant increase (usually greater than 10 fold) in the titer of antibody raised to the antigen. Enhancement of cellular immunity can be measured for example by a positive skin test, cytotoxic T-cell assay, ELISPOT assay for IFNg or IL-2. Preferably, the adjuvant in use in the invention is capable of stimulating immunity to the active agent, especially through toll-like receptors (TLR), such as TLR-7, TLR-8 and TLR-9. Representative examples of useful adjuvants include without limitation alum, mineral oil emulsion such as Freunds complete and incomplete (IFA), lipopolysaccharide or a derivative thereof (Ribi et al., 1986, Immunology and Immunopharmacology of Bacterial Endotoxins, Plenum Publ. Corp., NY, p 407-19), saponins such as QS21 (Sumino et al., 1998, J. Virol. 72, 4931-9; WO 98/56415), imidazoquinoline compounds such as Imiquimod (Suader, 2000, J. Am. Acad Dermatol. 43, S6-S11), 1H-imidazo(4,5-c)quinolon-4-amine derivative (Aldara™) and related compound (Smorlesi, 2005, Gene Ther. 12, 1324-32), cytosine phosphate guanosine oligodeoxynucleotides such as CpG (Chu et al., 1997, J. Exp. Med. 186: 1623; Tritel et al., 2003, J. Immunol. 171: 2358-2547) and cationic peptides such as IC-31 (Kritsch et al., 2005, J. Chromatogr Anal. Technol Biomed Life Sci 822, 263-70).

The composition of the invention can be in various forms, e.g. solid (e.g. dry powdered or lyophilized form), or liquid (e.g. aqueous). A solid composition of the active agent plus any additional desired ingredient(s) can be obtained from a previously sterile-filtered solution thereof submitted to vacuum drying and freeze-drying. It can, if desired, be stored in a sterile ampoule ready for reconstitution by the addition of a suitable vehicle before use.

The chimeric polypeptide, nucleic acid molecule, vector, infectious particle or composition of the invention can be administered by a variety of modes of administration, including systemic, topical and mucosal administration. Systemic administration can be performed by any means, e.g. by subcutaneous, intradermal, intramuscular, intravenous, intraperitoneal, intravascular, intraarterial injection. Injections can be made with conventional syringes and needles, or any other appropriate devices available in the art. Mucosal administration can be performed by oral, nasal, intratracheal, intrapulmonary, intravaginal or intra-rectal route. Topical administration can be performed using transdermal means (e.g. patch and the like). Intramuscular or subcutaneous administration is particularly preferred with viral vectors and infectious particles as active agent.

The appropriate dosage may vary depending upon known factors such as the pharmacodynamic characteristics of the particular active agent, age, health, and weight of the subject, the condition(s) to be treated, nature and extent of symptoms, kind of concurrent treatment, frequency of treatment, the need for prevention or therapy and/or the effect desired. The dosage will also be calculated dependent upon the particular route of administration selected. Further refinement of the calculations necessary to determine the appropriate dosage for treatment is routinely made by a practitioner, in the light of the relevant circumstances. For general guidance, suitable dosage for adenovirus particles varies from about $10^5$ to about $10^{13}$ iu (infectious units), desirably from about $10^7$ to about $10^{12}$ iu and preferably from about $10^8$ to about $10^{11}$ iu. Suitable dosage for vaccinia virus particles varies from about $10^4$ to about $10^{10}$ pfu (plaque-forming particle), desirably from about $10^5$ to about $10^9$ pfu and preferably from about $10^6$ to about $5 \times 10^8$ pfu. Vector plasmids can be administered in doses of between 10 µg and 20 mg, and preferably between 100 µg and 2 mg and chimeric polypeptide in doses between 05 µg to 5 g, preferably between 5 µg and 500 mg.

Further, the administration may take place in a single dose or, alternatively, in multiple doses according to standard protocols, dosages and regimens over several hours, days and/or weeks. Moreover, the administration can be by bolus injection or continuous infusion. For example, one may proceed by three sequential administrations at week interval followed by at leats one further administration within 4 to 6 months following the first series. As a general guidance, with a MVA vector as therapeutic agent, preferred administration route is subcutaneous with a dose of MVA particles comprised between $10^6$ to $5 \times 10^8$ pfu.

The chimeric polypeptide, nucleic acid molecule, vector, infectious particle, host cell or composition of the invention may be employed in methods for treating or preventing a variety of diseases and pathologic conditions, including genetic diseases, congenital diseases and acquired diseases. The present invention also pertains to the use of the chimeric polypeptide, vector, infectious particle, host cell or composition of the invention for the preparation of a drug intended for treating or preventing such diseases. It is particularly appropriate for treating or preventing infectious diseases (e.g. viral and/or bacterial infections), cancer and immune deficiency diseases. The term "cancer" encompasses any cancerous condition which results from unwanted cell proliferation including diffuse or localized tumors, metastasis, cancerous polyps and preneoplastic lesions (e.g. neoplasia). Cancers which are contemplated in the context of the invention include without limitation glioblastoma, sarcoma, melanoma, mastocytoma, carcinoma as well as breast cancer, prostate cancer, testicular cancer, ovarian cancer, endometrial cancer, cervical cancer (in particular, those associated with a papillomavirus infection), lung cancer (e.g. including large cell, small cell, squamous and adeno-carcinomas), renal cancer, bladder cancer, liver cancer, colon cancer, anal cancer, pancreatic cancer, stomach cancer, gastrointestinal cancer, cancer of the oral cavity, larynx cancer, brain and CNS cancer, skin cancer (e.g. melanoma and non-melanoma), blood cancer (lymphomas, leukemia, especially if they have developed in solid mass), bone cancer, retinoblastoma and thyroid cancer. Infectious diseases encompass those caused by any pathogenic microorganisms such as virus. Infectious diseases contemplated by the present invention include those associated with infection by a hepatitis virus (e.g. hepatitis A, B or C virus). Other Infectious diseases contemplated by the present invention include those associated with a papillomavirus (e.g. HPV-16, HPV-18, HPV-31, HPV-33, HPV-45, HPV-52) and such diseases include persistent infection, pre-malignant lesions (e.g. cervical intraepithelial neoplasia of low, moderate or high grade) and malignant lesions (e.g. cervical carcinoma).

The present invention also provides a method for recombinantly producing a polypeptide comprising the step of a) introducing in a host cell the vector or the infectious viral particle of the invention, b) culturing the transformed host cells under conditions that permit expression of the polypeptide of interest, and c) recovering and optionally purifying the polypeptide from the culture.

In one embodiment, the polypeptide is produced according to the method of the invention so as to be secreted in the extracellular medium. The polypeptide is preferably included in a chimeric polypeptide equipped with a signal peptide as described herein whereby the signal peptide is cleaved off from the chimeric polypeptide and the polypeptide recovered from the culture medium.

In another embodiment, the polypeptide is produced according to the method of the invention so as to be anchored to a cell membrane, with a special preference for attachment at the external surface of the plasma membrane. Preferably, the polypeptide is anchored in such a way that it can interact with other cell surfaces or other molecules present in the extracellular medium. The polypeptide is preferably included in a chimeric polypeptide equipped with a signal peptide and a membrane-peptide as described herein whereby the signal peptide is cleaved off from the chimeric polypeptide and the polypeptide recovered from the cultured cells.

The present invention also provides a method for directing expression of a polypeptide of interest extracellularly which comprises the steps of (a) generating a nucleic acid molecule by linking a first nucleotide sequence selected from the group consisting of SEQ ID NO: 11, SEQ ID NO: 12, SEQ ID NO: 13, SEQ ID NO: 14, SEQ ID NO: 15 and SEQ ID NO: 16 to a second nucleotide sequence encoding said polypeptide, wherein said nucleic acid molecule encodes a chimeric polypeptide comprising from N to C-terminus the signal peptide encoded by said first nucleotide sequence and the polypeptide of interest; (b) inserting the resulting nucleic acid molecule in an expression vector and (c) introducing said expression vector in a host cell or organism. As discussed before, the signal peptide is cleaved off from the chimeric polypeptide during secretion and the polypeptide of interest is then released extracellularly. It can be recovered from the culture medium and optionally purified using techniques conventional in the art.

The present invention also provides a method for directing expression of a polypeptide anchored at the surface of the plasma membrane which comprises the steps of (a) generating a nucleic acid molecule by inserting in a first nucleotide sequence selected from the group consisting of SEQ ID NO: 23, SEQ ID NO: 24, SEQ ID NO: 25, SEQ ID NO: 26, SEQ ID NO: 27 and SEQ ID NO: 28 a second nucleotide sequence encoding a polypeptide of interest at any position between the nucleotide in position 70 and the nucleotide in position 76 of said first nucleotide sequence, wherein said nucleic acid molecule encodes a chimeric polypeptide comprising N to C-terminus a signal peptide encoded by said first nucleotide sequence, the polypeptide of interest encoded by said second nucleic acid and a membrane-anchoring peptide encoded by said first nucleotide sequence; (b) inserting the resulting nucleic acid molecule in an expression vector and (c) introducing said expression vector in a host cell or organism. As discussed above, the signal peptide is cleaved off from the chimeric polypeptide and the polypeptide equipped with the membrane-anchoring peptide is presented at the surface of the expressing host cells in such a way that it can interact with other cell surfaces or other molecules present in the extracellular medium.

The nucleic acids, vectors, and polypeptides of the invention as described herein can be prepared (e.g., isolated, purified or synthesized) using routine methods known in the art, such as those described in, for example, Sambrook et al. (2001, Molecular Cloning, a Laboratory Manual, Cold Spring Harbor Press, Cold Spring Harbor, N.Y.), Ausubel et al. (1994, Current Protocols in Molecular Biology, Greene Publishing Associates and John Wiley & Sons, New York, N.Y.) and Herdewijn (2004, Oligonucleotide Synthesis: Methods and Applications (Methods in Molecular Biology), Humana Press, Totowa, N.J.).

The invention has been described in an illustrative manner, and it is to be understood that the terminology which has been used is intended to be in the nature of words of description rather than of limitation. Obviously, many modifications and variations of the present invention are possible in light of the above teachings. It is therefore to be understood that within the scope of the appended claims, the invention may be practiced in a different way from what is specifically described herein.

All of the above cited disclosures of patents, publications and database entries are specifically incorporated herein by reference in their entirety to the same extent as if each such individual patent, publication or entry were specifically and individually indicated to be incorporated by reference.

The following examples serve to illustrate the present invention.

EXAMPLES

The constructions described below are carried out according to the general genetic engineered and molecular cloning techniques detailed in the latest edition of Sambrook et al. (A Laboratory Manual, Cold Spring Harbor Laboratory Press, Cold Spring Harbor N.Y.) or according to the manufacturer's recommendations when a commercial kit is used. PCR amplification techniques are known to the person skilled in the art (see for example PCR protocols—A guide to methods and applications, 1990, published by Innis, Gelfand, Sninsky and White, Academic Press). The recombinant plasmids carrying the ampicillin resistance gene are replicated in the *E. coli* C600 (Stratagene), BJ5183 (Hanahan, 1983, J. Mol. Biol. 166, 557-580) and NM522 on agar or liquid medium supplemented with 100 µg/ml of antibiotic. The constructions of the recombinant vaccinia viruses are performed according to the conventional technology in the field in the documents above cited and in Mackett et al. (1982, Proc. Natl. Acad. Sci. USA 79, 7415-7419) and Mackett et al. (1984, J. Virol. 49, 857-864). The selection gene gpt (xanthine guanine phosphoribosyltransferase) of *E. coli* (Falkner and Moss, 1988, J. Virol. 62, 1849-1854) is used to facilitate the selection of the recombinant vaccinia viruses.

Example 1

Identification and Evaluation of New Signaling Sequences

It was shown that the presentation of antigens expressed by recombinant MVA was improved by the redirection of recombinant protein to the plasma membrane surface. Presentation at the plasma membrane requires that the gene of interest be cloned between sequences coding for a signal peptide and a membrane-anchoring peptide. Such signaling peptides are typically present in membrane-bound proteins, such as the rabies glycoprotein of various virus strains and have been widely used for expressing polypeptides of interest at the cell surface (see WO99/03885). More specifically, four different rabies virus strains are described and the amino acid sequence of the encoded glycoprotein available in specialized data bank, e.g. Uniprot available at NCBI, respectively under accession numbers M38452 (ERA strain) ay009097 (PG strain), S72465 (Nishigahara strain) and u11751 (artic fox strain). However, the combined use of the signaling peptides obtained from the glycoproteins of these available rabies strains is not appropriate in the context of multiple gene expression vectors when more than two recombinant polypeptides need to be addressed to the plasma membrane surface. Due to their high degree homology at the nucleotide level, homologous recombination events are likely to occur, which may negatively influence the vector stability and result in vector stocks improper for human use.

The present invention permits to solve this problem of potential homologous recombination and provides novel signaling peptides derived from the rabies glycoprotein and "degenerated" nucleotide sequences encoding such peptides that have been engineered so as to exhibit less than 75% of homology each other. These sequences were degenerated by modification of the codon usage pattern to reduce the DNA homologies, and thus limit the risk of recombination during vector production steps.

Six novel nucleotide sequences were engineered, encoding signal and membrane-anchoring peptides, that are named respectively M38452, v1 (SEQ ID NO: 23), ay009097, v1 (SEQ ID NO: 24), S72465, v1 (SEQ ID NO: 25), u11751, v1 (SEQ ID NO: 26), u11751, v2 (SEQ ID NO: 27) and M38452, v2-ay009097v2 (SEQ ID NO: 28). Table 1 shows the percentage of homologies exhibited by the nucleotide sequence of the invention encoding signal peptides whereas Table 2 illustrates the percentage of homologies exhibited by the nucleotide sequence of the invention encoding membrane-anchoring peptides.

A) Generation of the Nucleotide Sequences Encoding these New Signaling Sequences The nucleotides sequences were generated by assembling overlapping oligonucleotides. More specifically, in each case, two oligonucleotides were used for generating the signal peptide-encoding sequence and four oligonucleotides for the membrane-anchoring sequence. Each pair of synthetic sequences was then inserted in a PBS-derived vector, to provide pTG15833 (S72465, v1), pTG15834 (u11751, v1), pTG15835 (M38452, v1), pTG15943 (ay009097, v1), pTG15944 (M38452, v2-ay009097, v2) and pTG15945 (u11751, v2).

b) Evaluation of New Signaling Sequences

A non-oncogenic HPV-16 E7 protein (deleted of amino acid residues 21 to 26 (ΔDLYCYE) as described in WO99/03885) was used as a model protein to evaluate the capacity of the signal and membrane-anchored peptides encoded by each of the six sequence pairs to express a given polypeptide anchored to the plasma membrane. The nucleotide sequence encoding the HPV-16 E7 variant was cloned in each of the plasmids described above, in the BamHI site between the signal peptide-encoding sequence and the membrane-anchoring peptide sequence. In each case, expression was placed under the control of the vaccinia p7.5K promoter (Cochran et al, 1985. J. Virol. 54, 30-37). Expression and localization of E7 was then analysed after transient transfection of primary chicken embryos fibroblasts (CEF). $10^6$ cells, previously infected with MVATGN33.1 at an MOI of 1 pfu/cell, were transfected with 1 μg of plasmid DNA using Lipofectine (Invitrogen). 24 hours after transfection, E7 expression level was assayed by Western-blot analysis.

As a result, E7 was expressed at similar level from each of the tested plasmids except for pTG15833 which show a lower level of expression (sequence S72465v1 corresponding to SEQ ID NO: 25). It should be noted that the expression level is of the same order of magnitude as that observed with a control plasmid expressing E7 under the control of the signal and membrane-anchored peptides obtained from the glycoprotein of the reference rabies strain ERA (M38452).

Cell localisation was analyzed by immunofluorescence. $7.5 \times 10^4$ BHK21 cells were infected with MVATG33.1 at MOI of 1 pfu/cell and was then transfected with 0.125 μg of plasmid DNA, using Lipofectin (Invitrogen). After 24 hours, immunofluorescence was performed with a rabbit polyclonal anti-E7 antibody. E7 protein was detected on the plasma membrane surface for all the signaling sequences, as expected.

In conclusion, the novel signaling sequences could be used to express one or more polypeptide(s) of interest at the surface of the host cell anchored in plasma membrane.

TABLE 1

Percentage of DNA homologies between the sequences encoding the signal peptides disclosed herein

| | M38452 | M38452,v1 | ay009097,v1 | S72465,v1 | u11751,v1 | u11751, v2 |
|---|---|---|---|---|---|---|
| M38452,v1 | 71.0 | | | | | |
| ay009097,v1 | 71.0 | 71.0 | | | | |
| S72465,v1 | 66.7 | 66.7 | 68.1 | | | |
| rvu11751,v1 | 69.6 | 75.4 | 68.1 | 63.8 | | |
| rvu11751,v2 | 68.1 | 71.0 | 73.9 | 72.0 | 71.0 | |
| M38452,v2-ay009097v2 | 71.0 | 68.1 | 66.7 | 65.2 | 72.5 | 71.0 |

TABLE 2

Percentage of DNA homologies between the sequences encoding the membrane-anchoring peptides disclosed herein

| | M38452 | M38452,v1 | ay009097,v1 | S72465,v1 | u11751,v1 | u11751, v2 |
|---|---|---|---|---|---|---|
| M38452,v1 | 66.5 | | | | | |
| ay009097,v1 | 63.8 | 62.9 | | | | |
| S72465,v1 | 67.1 | 62.0 | 66.2 | | | |
| rvu11751,v1 | 62.4 | 62.4 | 62.4 | 62.0 | | |
| rvu11751,v2 | 60.1 | 62.4 | 59.6 | 65.2 | 67.6 | |
| M38452,v2-ay009097v2 | 59.6 | 56.3 | 64.8 | 71.3 | 63.8 | 60.5 |

The invention claimed is:

1. An isolated nucleic acid molecule comprising at least a nucleotide sequence encoding:
   (a) a membrane-anchoring peptide consisting of the amino acid sequence shown in SEQ ID NO:3 or
   (b) a chimeric polypeptide comprising a polypeptide of interest and
      (i) a membrane-anchoring peptide consisting of the amino acid sequence shown in SEQ ID NO: 3 or
      (ii) both a signal peptide consisting of the amino acid sequence shown in SEQ ID NO:1 or SEQ ID NO:2 and a membrane-anchoring peptide consisting of the amino acid sequence shown in SEQ ID NO:3.

2. The isolated nucleic acid molecule according to claim 1 comprising at least one of the nucleotide sequences shown in any of SEQ ID NOs:18, 22, 24, and 28.

3. The nucleic acid molecule as defined by claim 1 or claim 2, wherein the nucleotide sequence encoding a polypeptide of interest comprised in the chimeric polypeptide is inserted between approximately position 70 and approximately position 76 of SEQ ID NOs:24 or 28.

4. The nucleic acid molecule as defined by claim 1, wherein said nucleic acid molecule is placed under the control of appropriate regulatory elements in order to ensure its expression in a given host cell or organism.

5. A vector for expressing one or more chimeric polypeptide(s) comprising one or more nucleic acid molecule(s) as defined by claim 4.

6. The vector as defined by claim 5, comprising 2, 3, or 4 of said nucleic acid molecules.

7. The vector as defined by claim 6, wherein said 2, 3 or 4 nucleic acid molecules exhibit a percentage of homology between each other of less than 75%.

8. The vector as defined by claim 7, comprising the nucleotide sequence of SEQ ID NO: 24 to enable expression of a first polypeptide of interest to the cell membrane and the nucleotide sequence of SEQ ID NO: 28 to enable expression of a second polypeptide of interest to the cell membrane.

9. The vector as defined by claim 5, wherein said vector is a viral or a non viral vector.

10. The vector as defined by claim 9, wherein said vector is an adenoviral vector.

11. The vector as defined by claim 10, wherein said adenoviral vector is replication-defective.

12. The vector as defined by claim 9, wherein said vector is a poxviral vector.

13. The vector as defined by claim 12, wherein said poxviral vector is obtained from a vaccinia virus selected from the group consisting of the Copenhagen strain, the Wyeth strain, NYVAC and the highly attenuated Modified Vaccinia Ankara (MVA) strain.

14. An isolated host cell comprising the nucleic acid molecule as defined by claim 1 or the vector as defined by claim 5.

15. An immunogenic composition comprising the nucleic acid molecule encoding a chimeric polypeptide as defined by claim 1 or the vector as defined by claim 5 or the isolated host cell encoding a chimeric polypeptide as defined by claim 14 or any combination thereof and a pharmaceutically acceptable vehicle.

16. A method for inducing an immune response in a subject in need thereof, comprising the administration to said subject of the immunogenic composition of claim 15, the nucleic acid molecule encoding a chimeric polypeptide as defined by claim 1 or the vector encoding a chimeric polypeptide as defined by claim 5 or the isolated host cell comprising the nucleic acid encoding a chimeric polypeptide as defined by claim 14 or any combination thereof.

17. The method as defined by claim 16 wherein said immune response is induced to a pathogenic microorganism.

18. A method for recombinantly producing a polypeptide comprising the step of a) introducing in an isolated host cell the vector as defined by claim 5, b) culturing the transformed host cells under conditions that permit expression of the polypeptide of interest, and c) recovering and optionally purifying the polypeptide from the culture.

19. The nucleic acid molecule according to claim 1, wherein the signal peptide consisting of the amino acid sequence shown in SEQ ID NO:1 or SEQ ID NO:2 is linked at the amino terminus of the chimeric polypeptide.

20. The nucleic acid molecule according to claim 1, wherein the membrane-anchoring peptide consisting of the amino acid sequence shown in SEQ ID NO:3 is linked at the carboxy terminus or within the C-terminal portion of the polypeptide of interest.

21. The nucleic acid molecule according to claim 1, wherein the signal peptide consists of the amino acid sequence shown in SEQ ID NO:2.

22. The nucleic acid molecule according to claim 1, wherein said polypeptide of interest is selected from the group consisting of immunogenic polypeptides and anti-tumor polypeptides.

23. The nucleic acid molecule according to claim 22, wherein said immunogenic polypeptide is a papillomavirus polypeptide.

* * * * *

UNITED STATES PATENT AND TRADEMARK OFFICE
CERTIFICATE OF CORRECTION

| | | |
|---|---|---|
| PATENT NO. | : 8,415,462 B2 | Page 1 of 1 |
| APPLICATION NO. | : 12/600460 | |
| DATED | : April 9, 2013 | |
| INVENTOR(S) | : Nathalie Silvestre et al. | |

It is certified that error appears in the above-identified patent and that said Letters Patent is hereby corrected as shown below:

Title Page 1 of the patent, under Item 12 and the heading "(75) Inventors:"-

Please replace:

Nathalie Sylvestre with

--Nathalie Silvestre--.

On the Title Page:

The first or sole Notice should read --

Subject to any disclaimer, the term of this patent is extended or adjusted under 35 U.S.C. 154(b) by 470 days.

Signed and Sealed this
Eighteenth Day of June, 2013

Teresa Stanek Rea
*Acting Director of the United States Patent and Trademark Office*